(12) United States Patent
Eliseeva et al.

(10) Patent No.: US 10,669,288 B2
(45) Date of Patent: Jun. 2, 2020

(54) LANTHANIDE COMPLEXES BASED ON TRIETHYLENETETRAMINE-N,N,N',N'',N''', N''''-HEXAACETIC ACID DERIVATIVES

(71) Applicants: UNIVERSITE D'ORLEANS, Orlean (FR); Centre national de la recherche scientifique, Paris (FR)

(72) Inventors: Svetlana Eliseeva, Saint Jean le Blanc (FR); Franck Suzenet, La Chapelle Saint Mesmin (FR); Sylvain Routier, Tigy (FR); Raja Ben Othman, Chennevieres-sur-Marne (FR); Alexandra Collet, San Diego, CA (US); Ivana Martinic, Orleans (FR); Régis Delatouche, Orleans (FR); Stéphane Petoud, Paris (FR)

(73) Assignees: UNIVERSITE D'ORLEANS, Orleans (FR); CENTRE NATIONAL DE LA RECHERCHE SCIENTIFIQUE, Paris (FR)

(*) Notice: Subject to any disclaimer, the term of this patent is extended or adjusted under 35 U.S.C. 154(b) by 0 days.

(21) Appl. No.: 16/477,080

(22) PCT Filed: Jan. 10, 2018

(86) PCT No.: PCT/EP2018/050517
§ 371 (c)(1),
(2) Date: Jul. 10, 2019

(87) PCT Pub. No.: WO2018/130545
PCT Pub. Date: Jul. 19, 2018

(65) Prior Publication Data
US 2019/0330242 A1    Oct. 31, 2019

(30) Foreign Application Priority Data
Jan. 11, 2017  (FR) ...................... 17 50240

(51) Int. Cl.
*C07F 5/02*       (2006.01)
*A61K 49/00*    (2006.01)
*C07C 233/05*  (2006.01)

(52) U.S. Cl.
CPC ............ *C07F 5/022* (2013.01); *C07C 233/05* (2013.01); *A61K 49/0021* (2013.01); *A61K 49/0052* (2013.01)

(58) Field of Classification Search
CPC ................. C07F 5/022; C07C 233/05
See application file for complete search history.

(56) References Cited

U.S. PATENT DOCUMENTS 6,410,695 B1   6/2002   Sinn et al.
9,164,099 B2   10/2015  Gee et al.

FOREIGN PATENT DOCUMENTS

DE    19505960 A1    8/1996
WO    2004025259 A2  3/2004
WO    2018130545 A1  7/2018

OTHER PUBLICATIONS

Nishioka et al. "Minocycline-Based Europium(III) Chelate Complexes: Synthesis, Luminescent Properties, and Labeling to Streptavidin" Helvetica Chimica Acta, 2009, vol. 92, No. 11, pp. 2357-2374.*
Search Report for French Application No. 1750240 dated Jul. 12, 2017.
International Search Report and Written Opinion for PCT/EP2018/050517 dated Feb. 13, 2018.
Gee et al., "Site-Specific Labeling of Affinity Tags in Fusion Proteins", US2016025713 A1, Jan. 1, 2016 (Jan. 1, 2016), pp. 1-2, XP055389203.
Takuya et al, Minocycline-Based Europium (III) Chelate Complexes: Synthesis, Luminescent Properties, and Labeling to Streptavidin, Helevtica Chimica Acta—vol. 92, No. 11, Nov. 1, 2009, (Nov. 1, 2001), pp. 2357-2374, XP055389281.
Yao et al., "Time-Gated Detection of Cystathionine [gamma]—Lyase Activity and Inhibition with a Selective, Luminogenic Hydrogen Sulfide Sensor", Chemistry—A European Journal, vol. 23, No. 4, Nov. 25, 2016 ,(Nov. 25, 2016), pp. 752-756, XP055389283, ISSN: 0947-6539, DOI: 10.1002/chem.201604786.
Xiao M et al: "Quantum yields of luminescent lanthanide chelates and far-red dyes measured by resonance energy transfer", Journal of the American Chemical Society, American Chemical Society, US, vol. 123, No. 29, Jul. 25, 2004 (Jul. 25, 2004), pp. 7067-7073, XP009132321, ISSN: 0002-7863, DOI: 10.1021/JA0031669.

* cited by examiner

*Primary Examiner* — Joseph R Kosack
(74) *Attorney, Agent, or Firm* — Pearne & Gordon LLP

(57) ABSTRACT

The present invention relates to a complex comprising at least one lanthanide (Ln) and at least one compound (C) comprising a unit of formula (I) below:

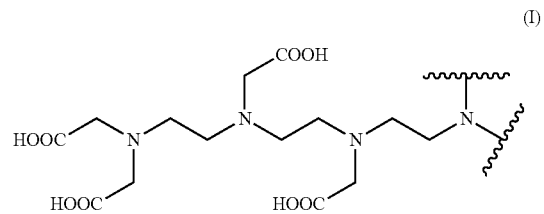

(I)

said unit of formula (I) being covalently connected to at least one antenna which absorbs at a wavelength ranging from 500 nm to 900 nm.

9 Claims, 6 Drawing Sheets

LANTHANIDE COMPLEXES BASED ON TRIETHYLENETETRAMINE-N,N,N',N",N'",N'"-HEXAACETIC ACID DERIVATIVES

CROSS-REFERENCE TO RELATED APPLICATIONS

This is the National Stage of PCT international application PCT/EP2018/050517, filed on Jan. 10, 2018, which claims the priority of French Patent Application No. 17 50240, filed Jan. 11, 2017, both of which are incorporated herein by reference in their entirety.

The present invention relates to lanthanide complexes based on triethylenetetramine-N,N,N',N",N'",N'"-hexaacetic acid derivatives. In particular, the subject of the present invention relates to compounds derived from triethylenetetramine-N,N,N',N",N'",N'"-hexaacetic acid, grafted to an antenna, capable of complexing with lanthanides.

The methods related to fluorescence (microscopy and macroscopy) have the advantages of being very sensitive, allowing real-time measurements, being little dangerous for biological media (because of the small quantity of imaging agents required subject to using suitable excitation wavelengths), and being very accessible (in terms of manufacturing costs and implementation), experimental time, mobility and degree of specialization of users.

The vast majority of commercial organic fluorophores are highly photosensitive and degrade in the presence of excitation light.

Fluorescent reporters based on semiconductor nanocrystals are another range of optical imaging agent choices. One of the limitations of use of these systems is the relatively large size of these nanoparticles that can interfere with the structures and functions of the cell. Another limiting factor is the high toxicity of the metals that make up these nanoparticles (cadmium, tellurium and selenium) in the case where the latter dissociate.

The family of lanthanides includes 14 elements with extremely interesting and unique optical properties, characterized by narrow and precise emission bands, ranging from visible to near infrared (>1200 nm). Each lanthanide has distinct and identifiable spectral properties. It is thus possible to identify, on the basis of the same technology, a whole range of different wavelengths by simply choosing the nature of the lanthanide to be incorporated in the molecule. These emission bands are much narrower than organic fluorophores and fluorescent nanoparticles (quantum dots), which allows for better spectral discrimination and multiplexed assays. In addition, the position (in nm) of these emission bands does not vary according to the environment (cell, pH, temperatures, hydrophilic/hydrophobic sites . . . ) which facilitates their detection and minimizes adaptation of the equipment (unique filter for a given lanthanide).

Despite the strong demand from biology researchers and physicians, there is currently no lanthanide-based fluorescent probe that is excitable and emits above 650 nm, thus corresponding to the biological window. Overall, current near-infrared probes are of an organic nature, while commercial probes are few and suffer from limitations such as the tendency towards photobleaching and restricted Stokes displacements.

The present invention therefore aims to provide a complex of lanthanides, of reduced size, emitting in the near infrared and that can be excited in the near infrared.

Another object of the invention is to provide a luminescent system emitting and absorbing in the near infrared and for observing various biological systems without destroying them.

Another object of the invention is to provide a luminescent system interacting little or not at all with biological materials, and thus limiting interference with the normal metabolism of biological systems.

The present invention relates to a complex comprising at least one lanthanide (Ln) and at least one compound (C) comprising a unit of formula (I) below:

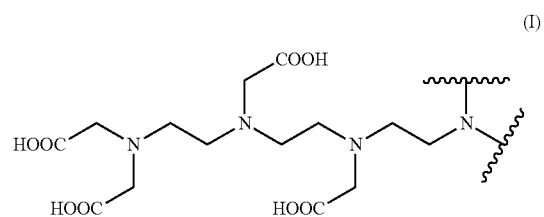

(I)

said unit of formula (I) being covalently connected to at least one antenna which absorbs at a wavelength ranging from 500 nm to 900 nm.

Among other advantages, luminescent compounds containing lanthanides have a spectral specificity in the visible and near infrared spectral discrimination due to their narrow emission bands specific to the nature of each lanthanide. In order to obtain a good luminescence intensity, it is important to introduce functional groups on the molecule that make it capable of absorbing a large amount of light radiation, and to transfer the resulting energy onto the luminescent lanthanide to obtain the emission of luminescence radiation by returning the lanthanide to the fundamental state.

Near infrared offers many unique advantages. It makes it possible to dispense with the auto-fluorescence of the tissues, and thus makes it possible to improve the signal-to-noise ratio and thus the detection sensitivity. Moreover, the biological tissues do not, or only little, absorb between 640 nm and 1100 nm (window of biological transparency), which allows an excitation of the probes at depth and non-invasive biological observation (diagnosis and research).

In addition, the lanthanide complexes are photostable. This photostability property is crucial in allowing the imaging agent to be excited i) over long experimental times and/or ii) during successive experiments and/or iii) by powerful excitation sources (lasers for confocal microscopy, for example). A larger amount of photons may thus be collected without disturbing or damaging the functioning of the biological system to be studied (it is important to remember here that the excitation wavelength (>650 nm) interacts extremely weakly with fluids and tissues and thus increases the intensity and quality of the signal collected.

The complexes according to the invention may be assimilated to probes possessing a chelating group of the TTHA type. Such probes have the advantage of being smaller with a lanthanide antenna. This small size allows for cell studies with minimization of the risk of interference with biological systems (cellular and whole organisms—no interference with normal metabolism). The flexibility of synthesis and the versatility in the functionalization of these probes, in particular with biological vectors, open the way to numerous applications and, in particular, the association with many biological vectors. Excitation at wavelengths greater than 650 nm minimizes the risk of disturbance of the system to be investigated by the excitation light.

The present invention thus relates to an entity obtained by complexation between a compound (C) as defined above and at least one lanthanide. The complexes thus obtained are luminescent molecules of small size, especially having a molar mass of less than 4 kDa.

The lanthanides are coordinated with the TTHA via the oxygen and nitrogen atoms with a coordination number which may be between 7 and 10. Thus, the coordination sphere of the lanthanide is completed and the metal is protected from its environment, in particular the solvent molecules.

The complexes according to the invention are obtained by placing a compound (C) in contact with a solution of lanthanides. The compound (C) is dissolved in a buffered solution at pH=8, while a solution of lanthanide salt is added to the solution containing the compound (C) in a one-to-one ratio.

Compound (C) comprises a unit of formula (I), said unit being derived from triethylenetetramine-N,N,N',N'',N''',N'''-hexaacetic acid (TTHA). According to one embodiment, in the compound (C), the unit of formula (I) is connected via an arm to an antenna as defined above.

The compounds (C) according to the invention may, for example, be represented by the following general formula:

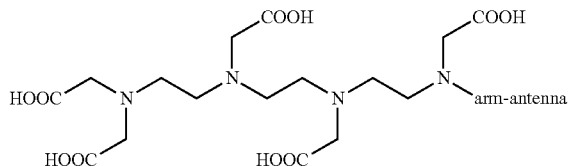

According to the invention, the term "antenna" refers to an entity capable of absorbing a large amount of excitation light to transfer the corresponding energy to the lanthanides.

Preferably, the antenna is selected from the group consisting of anthraquinones, cyanines, especially cyanines 5, cyanines 5,5 and cyanines 7, aza-BODIPY, perylenediimides, phenothiazine salts, and derivatives thereof.

According to the invention, the term "arm" refers to an entity for covalently connecting the unit of formula (I) and the antenna.

According to one embodiment, the antenna is connected to the unit of formula (I) in a covalent manner via an arm corresponding to the following formula (B):

in which:
i is 0 or 1;
j is an integer between 1 and 3;
X is chosen from the functions —NH—NH—CO—, thioester, ester, and amide, preferably from the ester and amide functions,
$A_1$ and $A_2$ are chosen, independently of one another, from linear or branched (cyclo)alkylene radicals comprising from 1 to 12 carbon atoms;
Z is selected from the: —O—, —NH—, —S—, amide, ester, triazole, amine, urea, thiourea, imine, oxyme, hydrazone, sulfonamide, carbamate, amidine, phosphoramidate, disulfide, and sulfonyl groups; and
Y is selected from the: —O—, —NH—, —S—, alkylene, amide, ester, triazole, amine, urea, thiourea, imine, oxyme, hydrazone, sulfonamide, carbamate, amidine, phosphoramidate, disulfide, and sulfonyl groups.

When Z (or Y) is an amide function, Z (or Y) may represent an —NH—CO— or —CO—NH— function. When Z (or Y) is an ester function, Z (or Y) may represent an —CO—O— or —O—CO— function.

According to one embodiment, Z (or Y) may represent the following triazole group:

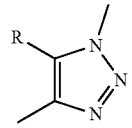

R representing a $(C_1-C_6)$alkyl or $(C_6-C_{10})$aryl group.

When Z (or Y) is an amine function, Z (or Y) may represent an —NH— or —N(R)— function, R representing a $(C_1-C_6)$alkyl or $(C_6-C_{10})$aryl group.

When Z (or Y) is a urea function, Z (or Y) may represent an —NH—CO—NH— function.

When Z (or Y) is a thiourea function, Z (or Y) may represent an —NH—CS—NH— function.

When Z (or Y) is an imine function, Z (or Y) may represent a —C(R)=N— or —N=C(R)— function, where R is a $(C_1-C_6)$alkyl or $(C_6-C_{10})$aryl group.

When Z (or Y) is an oxyme function, Z (or Y) may represent an —ON=C(R)— or —C(R)=NO— function, R representing a $(C_1-C_6)$alkyl or $(C_6-C_{10})$aryl group.

When Z (or Y) is a hydrazone function, Z (or Y) may represent an —NH—N=C(R)— or —C(R)=N—NH— function, R representing a $(C_1-C_6)$alkyl or $(C_6-C_{10})$aryl group.

When Z (or Y) is a sulfonamide function, Z (or Y) may represent an —NH—$SO_2$— or —$SO_2$—NH— function.

When Z (or Y) is a carbamate function, Z (or Y) may represent an —NH—CO—O— or —O—CO—NH— function.

When Z (or Y) is an amidine function, Z (or Y) may represent an —NH—C(=NH)— or —C(=NH)—NH— function.

When Z (or Y) is a phosphoramidate function, Z (or Y) may represent an —O—P(=O)OH—NH— function.

When Z (or Y) is a disulfide function, Z (or Y) may represent an —S—S— function.

When Z (or Y) is a sulphonyl function, Z (or Y) may represent an —SO2— function.

In the formula (B) as defined above, it is through the radical Y that the arm binds to the antenna and it is through X, or $A_1$ when i=0 that the arm binds to the formula (I) derived from TTHA.

Preferably, in formula (B), X is selected from the group consisting of the: —C(=O)—O—, —C(=O)—S—, —O—C(=O)—, —NH—C(=O)—, —N(Alk)-C(=O)—, —C(=O)—NH—, —NH—NH—C(=O)—, and —C(=O)—N(Alk)- groups, Alk representing an alkyl group having 1 to 6 carbon atoms.

Preferably, in the formula (B), i=0 and Z=—C(=O)—NH—.

Preferably, in the formula (B), $A_1$ and $A_2$ are chosen, independently of one another, from alkylene radicals, linear or branched, comprising from 1 to 4 carbon atoms.

Preferably, in formula (B), Z is selected from the group consisting of —O—, —NH—, —S—, —C(=O)—O—, —O—C(=O)—, —NH—C(=O)—, —N(Alk)-C(=O)—, —C(=O)—NH— and —C(=O)—N(Alk)- groups, Alk representing an alkyl group comprising 1 to 6 carbon atoms.

According to one embodiment, the compound (C) has the following formula (II):

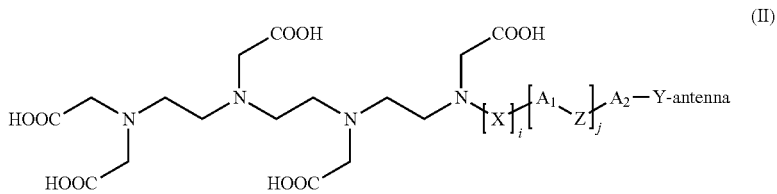
(II)

wherein i, j, $A_1$, $A_2$, X, Y and Z are as defined in formula (B) above.

Among the preferred compounds (C) according to the invention, mention may be made of compounds whose antenna is of the anthraquinone family.

The present invention relates, in particular, to complexes in which the compound (C) has the following formula (II-1):

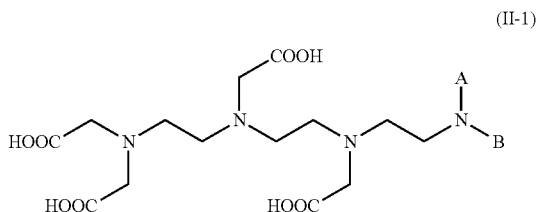
(II-1)

in which:
either A=—CH2-COOH and B=—(X)$_i$-[A$_1$-Z]$_j$-A$_2$-Y-AQ, AQ representing an anthraquinone unit and i, j, $A_1$, $A_2$, X, Y and Z being as defined in formula (B) above;
or A and B together with the nitrogen atom carrying them, forming a ring including an anthraquinone unit.

According to the invention, the term "anthraquinone unit" denotes a group derived from anthraquinone. It therefore denotes a polycyclic aromatic structure derived from anthraquinone of the formula below:

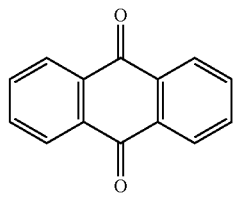 [SMILES: O=C1c2ccccc2C(=O)c2ccccc21]

This unit may therefore correspond to the above structure comprising one or more substituents such as OH, $NH_2$, NH(Alk), $N(Alk)_2$ or alkoxy groups, or else —NH-alkylene-$NH_2$ groups.

According to one embodiment, the compound (C) has the following formula (II-1):

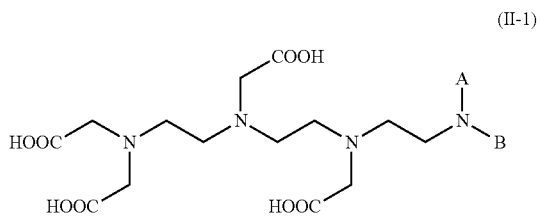
(II-1)

in which:
either A=—$CH_2$—COOH and B=—$CH_2$—C(O)—NH—$(CH_2)_2$—NH-AQ, AQ representing an anthraquinone unit;
or A and B together with the nitrogen atom carrying them form a ring including an anthraquinone unit.

According to one embodiment, the compound (C) has the following formula (III):

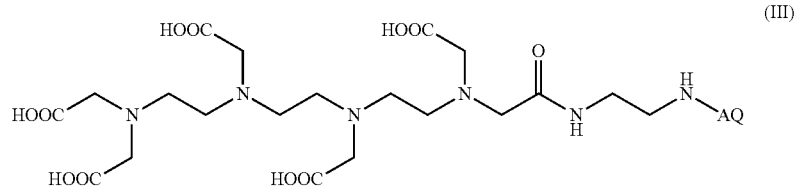
(III)

AQ representing an anthraquinone unit.

According to one embodiment, the compound (C) has the following formula (IV):

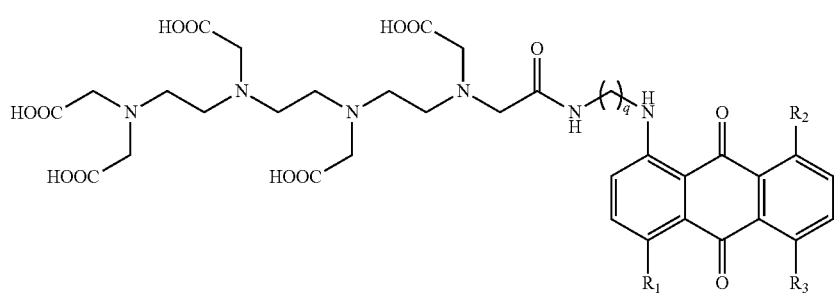
(IV)

q being an integer between 1 and 10;
$R_1$ representing:
  H;
  an —NH—$(CH_2)_n$—$NH_2$, group, where n is an integer between 1 to 6;
  an —NH—$(CH_2)_n$—$R_\alpha$, group, n being as defined above and $R_\alpha$ representing a group chosen from: halogens, carboxylic acids, succinimide esters, tetrafluorophenyl esters, acyl azides, anhydrides, acid halides, acrylamides, alcohols, amines, alkynes, cyclooctines, aminooxyacetamides, azides, imidoesters, sulfonate esters, haloacetamides, alkyl halides, sulfonyl halides, hydrazines, hydrazides, isocyanates, isothiocyanates, tetrazines, and maleimides;
  a ($C_1$-$C_6$)alkyl group;
  an $OR_a$ group, $R_a$ representing H or a ($C_1$-$C_6$)alkyl group;
  a $NR_aR_b$, group $R_a$ and $R_b$, identical or different, representing H or a ($C_1$-$C_6$)alkyl group; and $R_2$ and $R_3$, identical or different, representing:
  H;
  a ($C_1$-$C_6$)alkyl group;
  an $OR_a$ group, $R_a$ representing H or a group selected from ($C_1$-$C_6$)alkyl, ($C_6$-$C_{10}$)aryl and ($C_5$-$C_{10}$)heteroaryl groups;
  an —NH—$(CH_2)_n$—$R_\alpha$ group, n being as defined above and $R_\alpha$ being as defined above for $R_1$; and
  an $NR_aR_b$ group, $R_a$ and $R_b$, identical or different, representing H or a group selected from ($C_1$-$C_6$) alkyl, ($C_6$-$C_{10}$)aryl and ($C_5$-$C_{10}$)heteroaryl groups.

Preferably, in formula (IV) above, q=2.
Preferably, in formula (IV) mentioned above, $R_1$ represents OH or an —NH—$(CH_2)_n$—$NH_2$ group, n being as defined above.

According to one embodiment, in the aforementioned formula (IV), $R_1$ and $R_2$, identical or different, preferably identical, represent H or OH.

Preferably, the compound (C) corresponds to one of the following formulas:

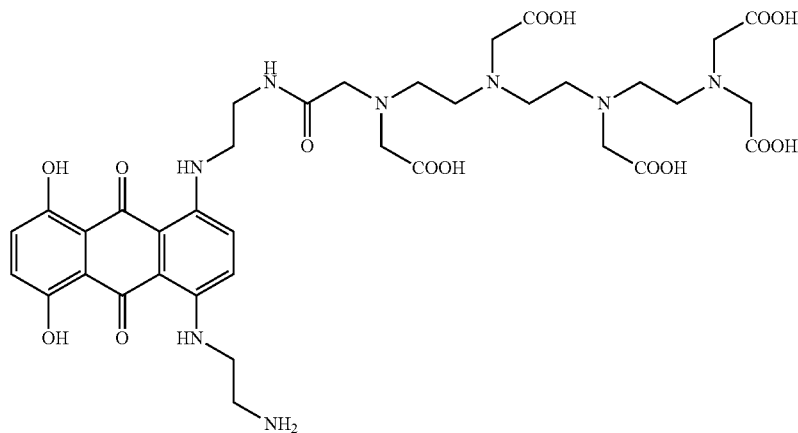

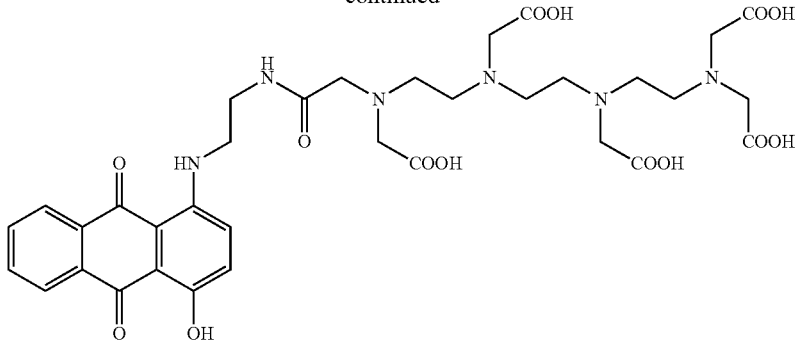

According to one embodiment, the compound (C) has the following formula (V):

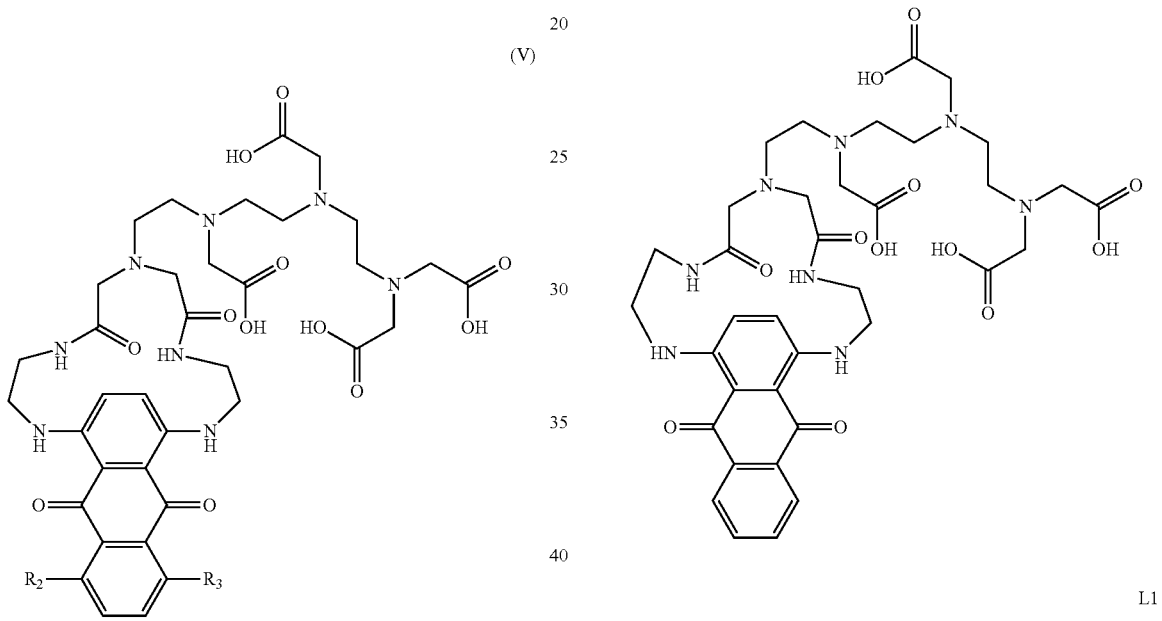

$R_2$ and $R_3$, identical or different, representing:

H;

a $(C_1-C_6)$alkyl group;

an $OR_a$ group, $R_a$ representing H or a group selected from $(C_1-C_6$alkyl, $(C_6-C_{10})$aryl and $(C_5-C_{10})$heteroaryl groups;

an $NR_aR_b$ group, $R_a$ et $R_b$, identical or different, representing H or a group selected from: $(C_1-C_6)$alkyl, $(C_6-C_{10})$aryl, and $(C_5-C_{10})$ heteroaryl groups.

Preferably, the compound (C) corresponds to one of the following formulas:

Among the compounds (C) that are preferred according to the invention, mention may be made of compounds whose antenna is of the aza-BODIPY family.

According to one embodiment, the compound (C) has the following formula (VI):

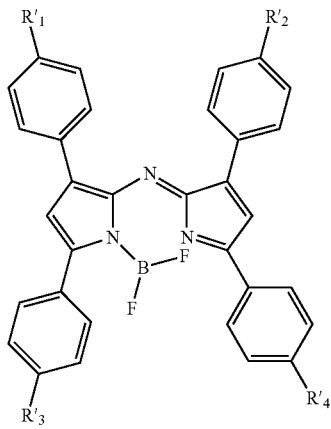
(VI)

in which:

R'$_1$ is H or is selected from the (C$_1$-C$_6$)alkyl, (C$_1$-C$_6$) alkoxy or NR$_a$R$_b$ groups, R$_a$ and R$_b$, identical or different, representing H or a (C$_1$-C$_6$)alkyl group;

R'$_2$ is:
either an —O-A$_3$-COOR$_a$ group, A$_3$ representing a (C$_1$-C$_6$)alkylene radical and R$_a$ representing H or a (C$_1$-C$_6$)alkyl group;
or a group of formula (VI-1) below:

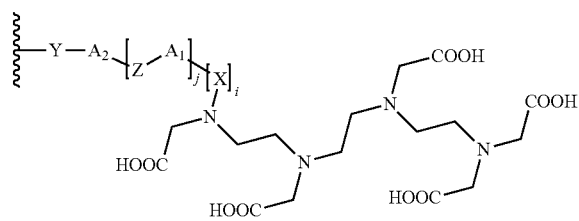
(VI-1)

in which i, j, X, A$_1$, A$_2$, Y and Z are as defined above in formula (B);

R'$_3$ is H or a group of formula (VI-1) mentioned above,

R'$_4$ is H or is selected from the (C$_1$-C$_6$)alkyl, (C$_1$-C$_6$) alkoxy or NR$_a$R$_b$ groups, R$_a$ and R$_b$, identical or different, representing H or a (C$_1$-C$_6$)alkyl group;

provided that when R'$_3$=H then R'$_2$ is a group of formula (VI-1) and when R'$_2$=—O-A$_3$-COOR$_a$ then R'$_3$ is a group of formula (VI-1).

In formula (VI), a group from R'$_2$ and R'$_3$ groups represents a group of formula (VI-1). In other words, the group R'$_2$ or the group R'$_3$ represents a group of formula (VI-1).

According to one embodiment, in formula (VI), R'$_2$ is a group of formula (VI-1) and R'$_3$ is H. According to one embodiment, R'$_2$ is an —O-A$_3$-COOR$_a$ group and R'3 is a group of formula (VI-1).

Among the groups of formula (VI-1) that are preferred, mention may be made of the following groups of formula (VI-2):

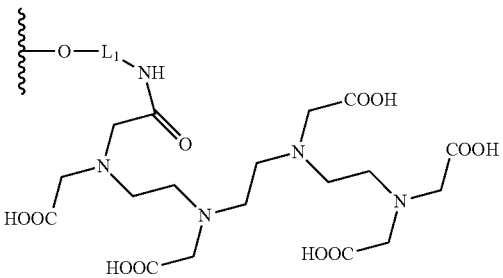
(VI-2)

L$_1$ representing a linker chosen from:
the —(CH$_2$)$_m$—C(=O)—NH—(CH$_2$)$_p$— radicals, m and p representing an integer between 1 and 4, and (C$_1$-C$_6$)alkylene radicals.

Preferably, in formula (VI) mentioned above, R'$_4$ is H.

According to one embodiment, in formula (VI), R'$_3$ may also be chosen from aryl, heteroaryl, amine, ether, alkyl or halogen groups.

According to one embodiment, the compound (C) has the following formula (VII):

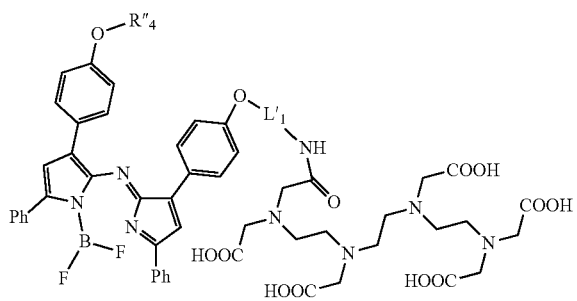
(VII)

in which:
L'$_1$ represents a —(CH$_2$)$_m$—C(=O)—NH—(CH$_2$)$_p$— radical, m and p representing an integer between 1 and 4, and
R''$_4$ represents a (C$_1$-C$_6$)alkyl group.

According to one embodiment, the compound (C) has the following formula (VIII):

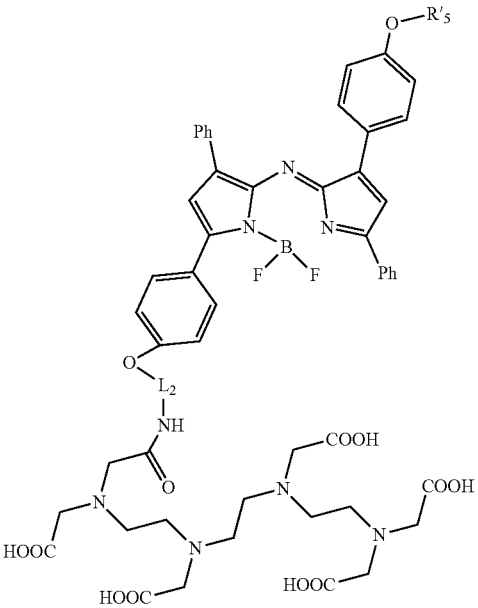
(VIII)

in which:
L$_2$ represents a (C$_1$-C$_6$)alkylene radical, and
R'$_5$ represents a (C$_1$-C$_6$)alkyl group, substituted by a COOR$_a$ group, R$_a$ representing H or a (C$_1$-C$_6$)alkyl group.

Among the preferred compounds of formula (VI), may be mentioned the following compounds:

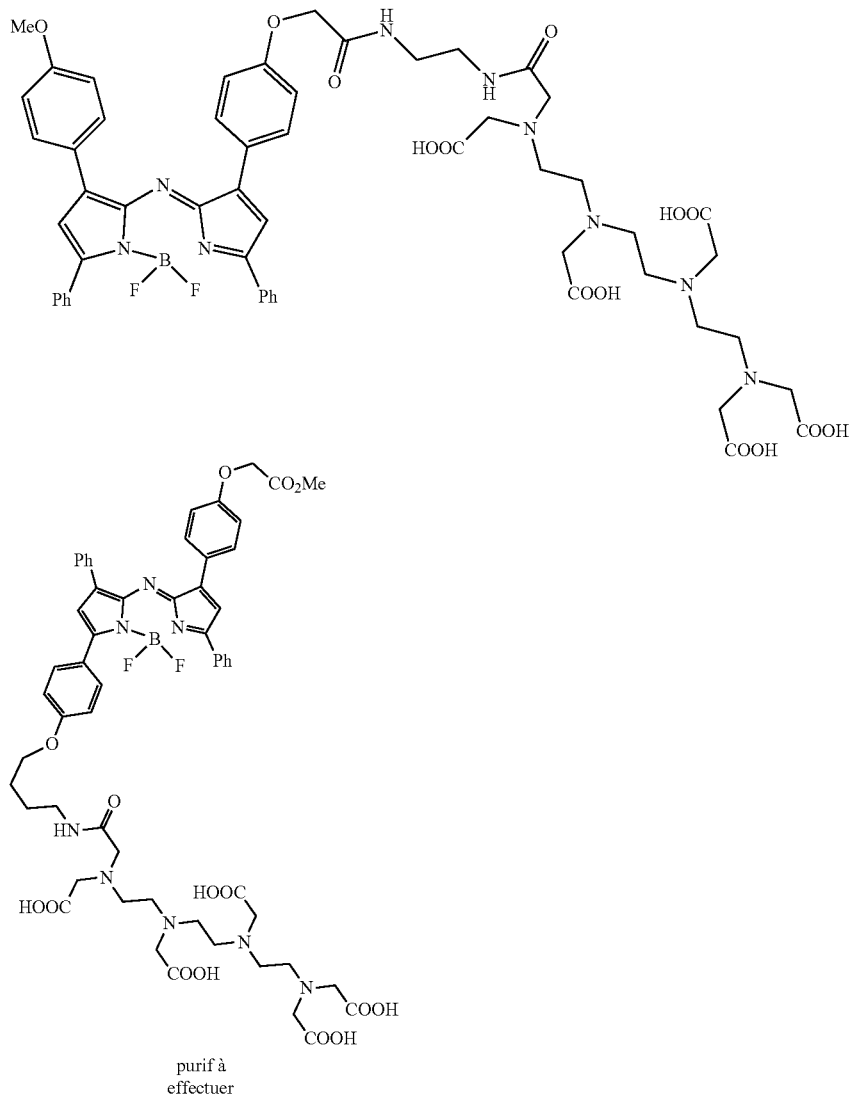

purif à effectuer

In the context of the present invention, the term "halogen atom" denotes fluorine, chlorine, bromine or iodine atoms.

According to the invention, the term "alkyl" refers to saturated, linear or branched hydrocarbon aliphatic groups comprising, unless stated otherwise, from 1 to 6 carbon atoms. By way of examples, mention may be made of methyl, ethyl, n-propyl, isopropyl, butyl, isobutyl, tert-butyl or pentyl groups.

In the context of the present invention, the term "(C$_1$-C$_6$) alkylene radical" means a bivalent radical, linear or branched, comprising from 1 to 6 carbon atoms, corresponding to an alkyl group with one hydrogen atom less.

According to the invention, the term "cycloalkyl" refers to cyclic carbon groups comprising, unless stated otherwise, from 3 to 6 carbon atoms. By way of examples, mention may be made of cyclopropyl, cyclobutyl, cyclopentyl or cyclohexyl groups.

According to the invention, the term "alkoxy" denotes an —O-alkyl radical where the alkyl group is as previously defined. By way of examples, mention may be made of the —O—(C$_1$-C$_4$)alkyl groups, and in particular the —O-methyl group, the —O-ethyl group, as the —O—C$_3$alkyl group, the —O-propyl, —O-isopropyl group, and as the —O—C$_4$alkyl group, the —O-butyl, —O-isobutyl, —O-tertbutyl group.

According to the invention, the term "(hetero)aryl" embraces both the terms "aryl" and "heteroaryl", these terms being as defined hereinafter.

According to the invention, the aryl groups are cyclic aromatic groups comprising between 6 and 10 carbon atoms. As examples of aryl groups, mention may be made of phenyl or naphthyl groups.

According to the invention, the term "heteroaryl" denotes a 5- to 10-membered monocyclic or bicyclic aromatic group containing from 1 to 4 heteroatoms selected from 0, S or N.

According to the invention, the term bicyclic heteroaryl includes fused aromatic bicycles.

By way of examples, may be mentioned imidazolyl, thiazolyl, oxazolyl, furanyl, thiophenyl, pyrazolyl, oxadiazolyl, tetrazolyl, pyridinyl, pyrazinyl, pyrimidinyl, pyridazinyl, indolyl, benzofuranyl, benzothiophenyl, benzoxazolyl, benzimidazolyl, indazolyl, benzothiazolyl, isobenzothiazolyl groups, benzotriazolyl, quinolinyl, isoquinolinyl.

As examples of heteroaryl comprising 5 or 6 atoms, including 1 to 4 nitrogen atoms, may be mentioned the following representative groups: pyrrolyl, pyrazolyl, 1,2,3-triazolyl, 1,2,4-triazolyl, tetrazolyl and 1,2,3-triazinyl.

Mention may also be made, as examples of heteroaryl, thiophenyl, oxazolyl, furazanyl, 1,2,4-thiadiazolyl, naphthyridinyl, quinoxalinyl, phthalazinyl and imidazo [1,2-a] pyridine. imidazo [2,1-b] thiazolyl, cinnolinyl, benzofurazanyl, azaindolyl, benzimidazolyl, benzothiophenyl, thienopyridyl, thienopyrimidinyl, pyrrolopyridyl, imidazopyridyl, benzoazaindole, 1,2,4-triazinyl, indolizinyl, isoxazolyl, isoquinolinyl, isothiazolyl, purinyl, quinazolinyl, quinolinyl, isoquinolyl, 1,3,4-thiadiazolyl, thiazolyl, isothiazolyl, carbazolyl, as well as the corresponding groups resulting from their fusion or from the fusion with the phenyl nucleus.

According to one embodiment, in the complexes according to the invention, the lanthanide is chosen from the group consisting of Yb, Nd, Ho, Tm, Sm, Dy, Eu, Pr and Er. The lanthanide content respects the stoichiometry of a lanthanide cation per molecule of TTHA.

The present invention also relates to a conjugate comprising a biological molecule and a complex as defined above, wherein said complex is linked to the biological molecule via a linker, said biological molecule being chosen from the group consisting of antibodies, proteins, peptides, carbohydrates, lipids, polysaccharides, fatty acids, amino acids, deoxyribonucleic acids, ribonucleic acids, oligonucleotides, drugs and ligands.

The present invention also relates to the use of a complex as defined above as a fluorescent chromophore.

According to the invention, the term "fluorescent chromophore" refers to a molecule that can re-emit light after excitation with a quantum yield greater than $10^{-6}$ ($10^{-4}$%).

The complexes according to the invention may, in particular, be used in the field of cell imaging, veterinary imaging, blood tests, biopsies, histological section analyzes, high throughput screening assays, bioanalytical assays on plates with 96, 396 and 10536 wells or assisted surgery (guided) by imaging.

EXAMPLES

Figure 1:
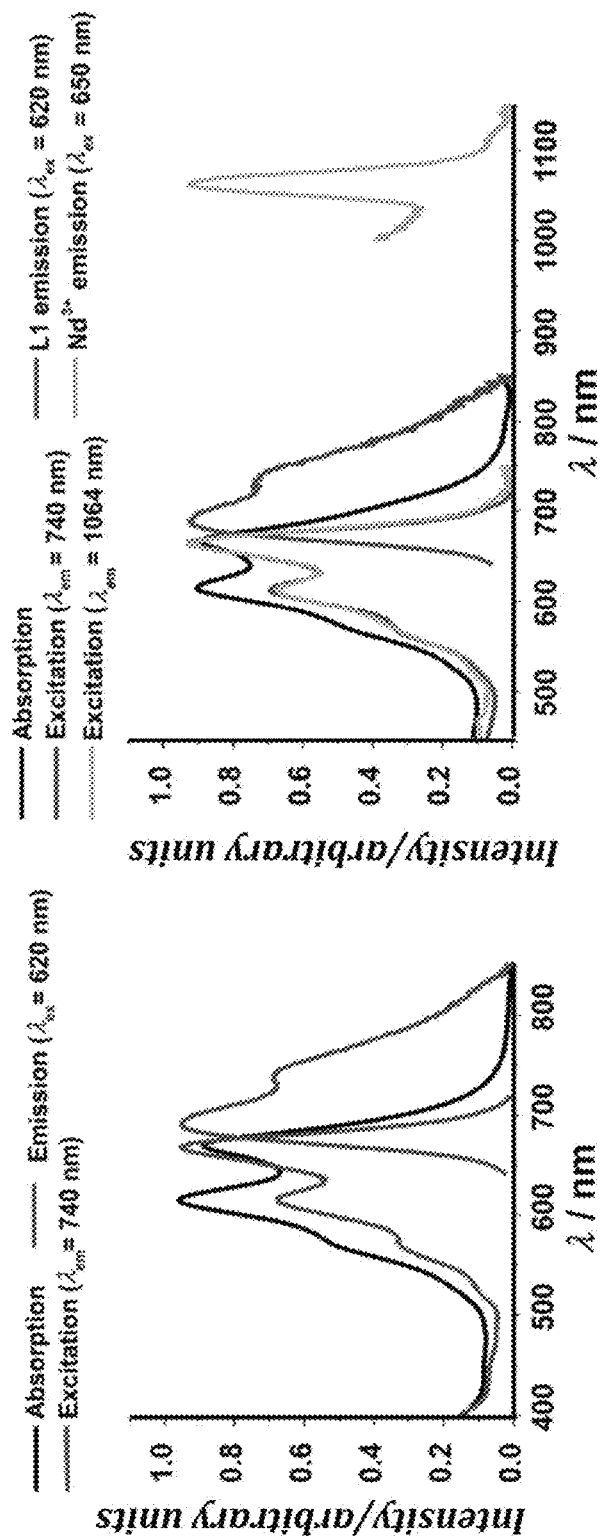
FIG. 1 shows the normalized absorption, excitation and emission spectra of ligand L1 (left) and L1Nd$^{3+}$ complex (right, 100 µM, HEPES buffer, pH=7.5, measured at room temperature).

Example 1: Synthesis of Compounds (C) According to the Invention

1. Preparation of Antennas of the Aza-BODIPY Type 1.1. Preparation of tert-butyl N-[2-[[2-[4-[(2Z)-2-[1-difluoroboranyl-3-(4-methoxyphenyl)-5-phenyl-pyrrol-2-yl]imino-5-phenyl-pyrrol-3-yl]phenoxy]acetyl]amino]ethyl]carbamate (10)

This antenna (10) is obtained according to the reaction scheme below:

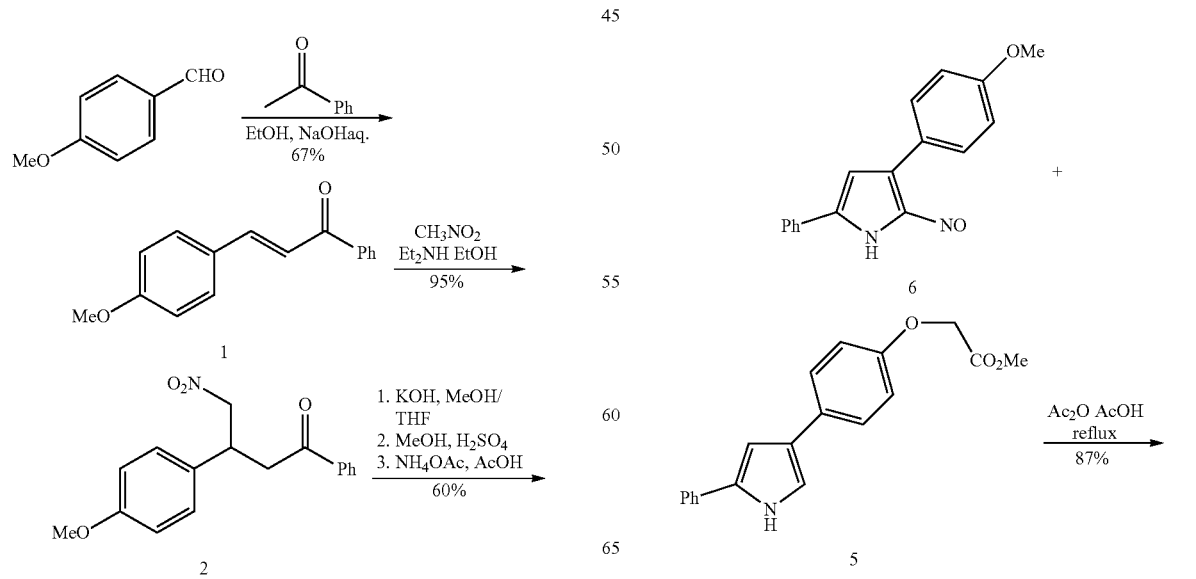

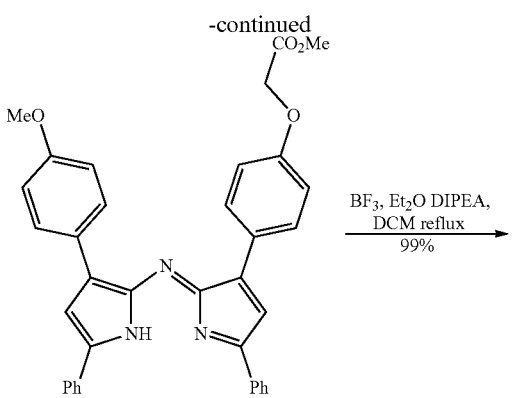

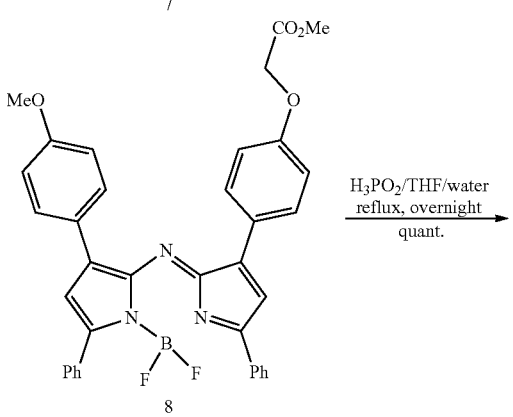

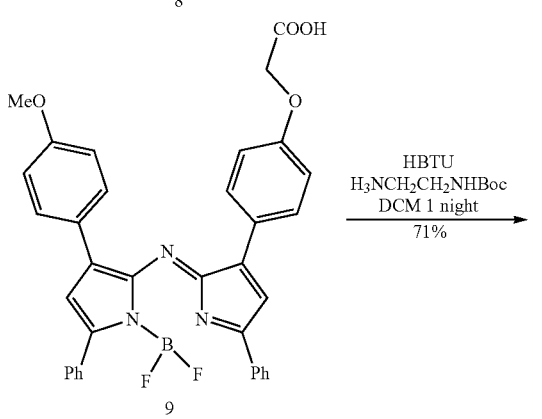

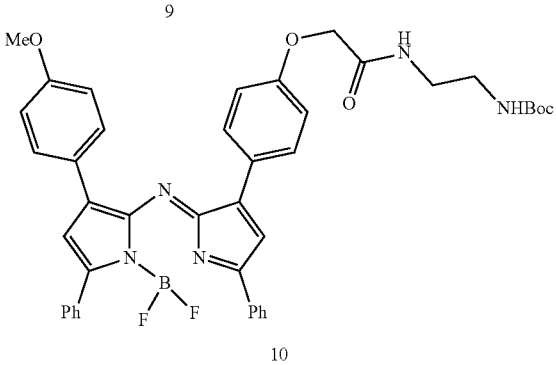

Synthesis of (E)-3-(4-methoxyphenyl)-1-phenyl-prop-2-en-1-one (1)

8.94 ml of para-anisaldehyde (Sigma) (10 g, 73.45 mmol, 1 eq.) and 8.58 ml of acetophenone (Sigma) (8.825 g, 73.45 mmol, 1 eq.) are dissolved in a flask in 150 mL of ethanol. The flask is immersed in an ice bath and 5.876 g of sodium hydroxide (149.9 mmol, 2 eq.) dissolved in 50 ml of water are added dropwise. The solution is allowed to warm to room temperature and stirred overnight. The next day, the flask is immersed in an ice bath and cold water is added to the mixture. A yellow precipitate forms and the mixture is sintered and washed with water. The precipitate is then recrystallized from ethanol yielding 11.698 g of chalcone 1 (49.1 mmol, 67%) as white crystals.

$^1$H NMR (250 MHz, Chloroform-d) δ 8.06-7.97 (m, 2H), 7.79 (d, J=15.0 Hz, 1H), 7.64-7.59 (m, 2H), 7.58-7.45 (m, 3H), 7.42 (d, J=15.6 Hz, 1H), 6.98-6.91 (m, 2H), 3.86 (s, 3H).

Synthesis of 3-(4-methoxyphenyl)-4-nitro-1-phenylbutan-1-one (2)

0.546 g (2.29 mmol, 1 eq.) of 0.621 mL of nitromethane (Sigma) (11.46 mmol, 5 eq.) and 1.185 mL of diethylamine (Sigma) (11.46 mmol) are dissolved in a flask in 150 mL of methanol. The solution is heated to reflux overnight. After the reaction is complete, the solvent is evaporated in vacuo and the residue dissolved in dichloromethane. The solution is washed with a solution of 1M KHSO$_4$ then saturated NaCl. The organic phases are combined, dried over MgSO$_4$, filtered and concentrated in vacuo. The residue is purified by chromatography on silica with petroleum ether/ethyl acetate providing nitrobutanone 2 (0.654 g, 2.18 mmol, 95%) as a pale yellow viscous oil.

$^1$H NMR (250 MHz, Chloroform-d) δ 7.96-7.88 (m, 2H), 7.63-7.53 (m, 1H), 7.51-7.41 (m, 2H), 7.25-7.16 (m, 2H), 6.91-6.81 (m, 2H), 4.80 (ddd, J=12.3, 6.7, 0.5 Hz, 1H), 4.65 (ddd, J=12.3, 7.9, 0.4 Hz, 1H), 4.18 (p, J=7.0 Hz, 1H), 3.78 (s, 3H), 3.42 (dd, J=7.0, 2.1 Hz, 2H).

Synthesis of 4-(4-methoxyphenyl)-2-phenyl-1H-pyrrole (3)

In a flask are dissolved 3.5 g of nitrobutanone 2 (11.69 mmol, 1 eq.) and 5 eq. of KOH in 100 mL of MeOH/THF (1:2). The solution is stirred at room temperature for one hour and then added dropwise to a solution of concentrated H$_2$SO$_4$ (2 mL/mmol) dissolved in 100 mL of MeOH at 0° C. After the addition is complete, the ice bath is removed and the solution stirred at room temperature for 1 h. The mixture is then poured into an Erlenmeyer flask containing water and ice and the solution is neutralized by adding a 4M sodium hydroxide solution. Once neutralized, the mixture is extracted with dichloromethane and the organic phase is dried over MgSO$_4$, filtered and the solvent evaporated under reduced pressure. The residue is dissolved in 100 mL glacial acetic acid and 5 eq. ammonium acetate (Sigma) are added. The solution is heated at reflux for one hour during which the color of the solution changes from yellow to deep blue. The solution is cooled to room temperature and the acetic acid evaporated under reduced pressure. The black solid is then dissolved in dichloromethane and the solution is washed several times with a saturated solution of sodium bicarbonate and brine. The organic phase is dried over MgSO$_4$, filtered and concentrated under reduced pressure. The residue is then dissolved in a minimum of dichloromethane and the petroleum ether is added slowly until a precipitate forms. The precipitate is filtered on Buchner and washed several times with petroleum ether. Pyrrole 3 is obtained with a yield of 60% (1742 g, 6.99 mmol) in the form of a slightly colored powder.

$^1$H NMR (250 MHz, DMSO-d$_6$) δ 11.32 (s, 1H), 7.66 (dt, J=7.7, 1.1 Hz, 2H), 7.57-7.48 (m, 2H), 7.36 (dd, J=8.4, 7.0 Hz, 2H), 7.21 (dd, J=2.8, 1.7 Hz, 1H), 7.20-7.12 (m, 1H), 6.94-6.84 (m, 3H), 3.75 (s, 3H).

Synthesis of 4-(5-phenyl-1H-pyrrol-3-yl) phenol (4)

0.546 g of pyrrole 3 (2.19 mmol, 1 eq.) are dissolved in a flask under argon in 100 ml of anhydrous dichloromethane. The solution is cooled to −78° C. and 5.48 ml of a solution of 1M BBr$_3$ in dichloromethane (Sigma) (5.48 mmol, 2.5 eq.) are slowly added. The reaction is stirred for 3 h at −78° C. and then overnight at room temperature. The next day, the solution is cooled to −78° C. and MeOH is added to the mixture. The solution is stirred for one hour then it is diluted in dichloromethane and washed with saturated NaCl. The organic phase is dried over MgSO$_4$, filtered and concentrated under reduced pressure. The residue is dissolved in a minimum of dichloromethane and the product is precipitated by slow addition of petroleum ether. The precipitate is filtered on Buchner and washed with petroleum ether yielding 0.495 g (2.10 mmol, 96%) of pyrrole 4 in the form of a slightly purplish white powder.

$^1$H NMR (250 MHz, DMSO-d$_6$) δ 11.25 (s, 1H), 9.15 (s, 1H), 7.69-7.61 (m, 2H), 7.43-7.31 (m, 4H), 7.20-7.11 (m, 2H), 6.81 (dd, J=2.7, 1.7 Hz, 1H), 6.77-6.69 (m, 2H).

$^1$H NMR (250 MHz, acetone-d$_6$) δ 10.48 (s, 1H), 8.09 (s, 1H), 7.71-7.65 (m, 2H), 7.49-7.41 (m, 2H), 7.41-7.31 (m, 2H), 7.21-7.14 (m, 2H), 6.85 (dd, J=2.8, 1.7 Hz, 1H). 6.84-6.80 (m, 2H).

$^{13}$C NMR (63 MHz, acetone) δ 156.27, 134.16, 133.40, 129.58, 128.76, 126.92, 126.80, 126.55, 124.38, 116.24, 115.94, 104.14.

LRMS: calcd: 235.0997, measured [M+H]$^+$: 236.1

IR (cm$^{-1}$): 3443, 3300, 1600, 1581, 1494, 1244, 1132, 921, 834, 804, 778, 751, 717, 690, 609.

Mp: 209° C.

Synthesis of methyl 2-(4-(5-phenyl-1H-pyrrol-3-yl) phenoxy) acetate (5)

0.725 g of 4 (3.08 mmol, 1 eq.) in 60 ml of DMF are dissolved in a flask. 1.278 g of K$_2$CO$_3$ (9.24 mmol, 3 eq.), 1.08 ml of methyl chloroacetate (Sigma) (12.33 mmol, 4 eq.) and a catalytic amount of potassium bromide are added to the solution which is stirred at room temperature overnight. The solution is then extracted with diethyl ether and washed three times with brine. The aqueous phase is then extracted three times with diethyl ether. The organic phases are combined and dried over MgSO$_4$, filtered and the solvent evaporated in vacuo. The residue is dissolved in a minimum of dichloromethane and petroleum ether is added until a precipitate forms. The precipitate is filtered through Buchner and washed with petroleum ether to give 0.553 g of 5 as an off-white powder.

$^1$H NMR (250 MHz, Chloroform-d) δ 8.43 (s, 1H), 7.55-7.46 (m, 4H), 7.44-7.35 (m, 2H), 7.25-7.19 (m, 1H), 7.07 (dd, J=2.7, 1.7 Hz, 1H), 6.97-6.88 (m, 2H), 6.76 (dd, J=2.8, 1.7 Hz, 1H), 4.66 (s, 2H), 3.82 (s, 3H).

$^{13}$C NMR (63 MHz, CDCl$_3$) δ 169.57, 156.10, 133.02, 132.51, 129.56, 128.93, 126.45, 126.38, 126.11, 123.83, 114.98, 114.86, 65.58, 52.25.

LRMS: Calcd: 307.1208, Measured [M+H]$^+$: 308.4

IR (cm$^{-1}$): 3430, 2941, 1759, 1600, 1581, 1496, 1438, 1212, 1178, 1131, 1075, 834, 801, 774, 758, 719, 693.

Mp: 165° C.

Synthesis of 3-(4-methoxyphenyl)-2-nitroso-5-phenyl-1H-pyrrole (6)

0.593 g of pyrrole 3 (2.38 mmol, 1 eq.) in 50 ml of ethanol and 0.48 ml of concentrated HCl (0.2 ml/mmol) are dissolved in a flask at room temperature. 0.189 g of sodium nitrite (2.74 mmol, 1.15 eq.) dissolved in water (concentration 0.6 mol/l) are added dropwise. The solution is stirred for 30 min and is then cooled to 0° C. A second portion of concentrated HCl (2.38 mL, 1 mL/mmol) is added. The solution is stirred for one hour and then dissolved in dichloromethane and washed with brine. The organic phase is dried, filtered and concentrated under reduced pressure. The residue is dissolved in a minimum volume of ethanol and excess aqueous solution of sodium acetate and ice are added and the mixture is stirred for one hour. The solution is then extracted with dichloromethane and washed with brine. The organic phase is dried over MgSO$_4$, filtered and concentrated in vacuo. The residue is then dissolved in a minimum volume of dichloromethane and the product is precipitated by slow addition of petroleum ether. The solid is filtered on Buchner and washed with petroleum ether. 0.503 g of nitrosopyrrole 6 (1.81 mmol, 76%) are obtained in the form of a green powder.

$^1$H NMR (250 MHz, Chloroform-d) δ 8.20-8.13 (m, 2H), 7.79 (dd, J=6.9, 3.0 Hz, 2H), 7.51 (dd, J=5.1, 1.8 Hz, 3H), 7.07 (s, 1H), 7.02 (d, J=8.9 Hz, 2H), 3.89 (s, 3H).

Synthesis of (Z)-methyl2-(4-(2-((3-(4-methoxyphenyl)-5-phenyl-1H-pyrrol-2-yl)imino)-5-phenyl-2H-pyrrol-3-yl)phenoxy)acetate (7)

20 g of glacial acetic acid (0.112 g of nitrosopyrrole 6 (0.40 mmol, 1 eq.), 0.124 g of pyrrole (0.40 mmol, 1 eq. 0.40 mL of acetic anhydride. The solution is stirred and heated at reflux for one hour during which the color changes to dark blue. The solution is then cooled and the solvent evaporated under reduced pressure. The residue is then dissolved in dichloromethane and the solution is washed with saturated NaHCO$_3$ and saturated NaCl. The organic phase is dried over MgSO$_4$, filtered and concentrated in vacuo. The residue is then dissolved in a minimum of dichloromethane and the petroleum ether is added until a precipitate forms which is filtered on Buchner and washed with petroleum ether. Azadipyrromethene 7 is obtained in the form of a dark blue powder (0.197 g, 0.35 mmol, 87%).

$^1$H NMR (250 MHz, Chloroform-d) δ 8.05-7.98 (m, 4H), 7.93 (ddd, J=7.8, 6.4, 1.5 Hz, 4H), 7.58-7.44 (m, 7H), 7.11 (s, 1H), 7.09 (s, 1H), 6.96 (dd, J=8.9, 1.8 Hz, 4H), 4.71 (s, 2H), 3.90 (s, 3H), 3.85 (s, 3H).

IR (cm$^{-1}$): 3426, 2948, 1758, 1597, 1495, 1211, 1175, 1075, 1002, 902, 833, 801, 772, 759, 745, 718, 692, 637, 605. Mp: 230° C.

HRMS (ESI): m/z calcd for [C$_{36}$H$_{30}$N$_3$O$_4$]: 568.223083, measured 568.222834 (−0.4 ppm)

Synthesis of (Z)-methyl2-(4-(2-((1-(difluoroboryl)-3-(4-methoxyphenyl)-5-phenyl-1H-pyrrol-2-yl) imino)-5-phenyl2H-pyrrol-3-yl)phenoxy)acetate (8)

In a flask under argon are dissolved 0.183 g of azadipyrromethene 7 (0.32 mmol, 1 eq.) and 0.548 ml of DIPEA (Sigma) (3.22 mmol, 10 eq.) in freshly distilled dichloromethane. After stirring for a few minutes at room temperature, 0.613 ml of distilled BF$_3$.Et$_2$O (Sigma) (4.84 mmol, 15 eq.) are added and the solution is refluxed for two hours. The solution is then cooled to room temperature and the organic phase is washed with brine three times. The aqueous phase is then re-extracted three times with dichloromethane and the combined organic phases are dried over MgSO$_4$, filtered and concentrated in vacuo. The residue is purified by chromatography on silica with a gradient of PE/DCM. Azabodipy 8 is obtained as an iridescent dark blue powder (0.196 g, 0.318 mmol, 99%).

$^1$H NMR (400 MHz, Acetone-d$_6$) δ 8.23 (dd, J=8.8, 6.2 Hz, 4H), 8.18-8.09 (m, 4H), 7.58-7.46 (m, 6H), 7.33 (d, J=1.4 Hz, 2H), 7.14 (dd, J=9.0, 7.2 Hz, 4H), 4.88 (s, 2H), 3.92 (s, 3H), 3.79 (s, 3H).

$^{13}$C NMR (101 MHz, acetone) δ 169.66, 162.39, 160.53, 132.72, 131.94, 131.87, 131.70, 131.62, 130.55, 130.51, 129.36, 125.87, 118.92, 115.83, 115.26, 65.70, 55.88, 52.29.

$^{19}$F NMR (235 MHz, Acetone-d$_6$) δ −130.38 (dd, J=62.8-31.4 Hz).

HRMS (ESI): m/z calcd for [C$_{36}$H$_{29}$BF$_2$N$_3$O$_4$]: 616.221996, measured 616.221217 (−1.3 ppm)

Mp: 179° C.

IR (cm$^{-1}$): 3288, 2918, 2584, 1758, 1728, 1601, 1504, 1487, 1454, 1388, 1277, 1252, 1228, 1175, 1129, 1100, 1068, 1024, 999, 970, 929, 904, 868, 836, 818, 767, 742, 690, 641, 615.

Synthesis of (Z)-2-(4-(2-((1-(difluoroboryl)-3-(4-methoxyphenyl)-5-phenyl-1H-pyrrol-2-yl)imino)-5-phenyl-2H-pyrrol-3-yl)phenoxy) acetic acid (9)

0.308 g of azabodipy 8 (0.5 mmol, 1 eq.) in a THF/water/H$_3$PO$_4$ mixture (50 ml: 25 ml: 10 ml) is dissolved in a flask. The solution is stirred under reflux for 20 hours until no trace of the ester is visible by TLC. After cooling, the solution is extracted with dichloromethane. The organic phase is washed with brine and then the aqueous phases are re-extracted with dichloromethane until no blue color is observed in the aqueous phase. The organic phase is dried over MgSO$_4$, filtered and concentrated under reduced pressure. The residue can optionally be purified by chromatography with DCM/MeOH if the ester is still present in the crude. Azabodipy 9 is obtained as a dark blue solid (0.294 g, 0.49 mmol, 98%).

$^1$H NMR (250 MHz, Acetone-d$_6$) δ 8.27-8.18 (m, 4H), 8.18-8.09 (m, 4H), 7.57-7.48 (m, 6H), 7.32 (d, J=1.8 Hz, 2H), 7.19-7.08 (m, 4H), 4.86 (s, 2H), 3.91 (s, 3H).

HRMS (ESI): m/z calcd for [C$_{35}$H$_{27}$BF$_2$N$_3$O$_4$]: 602.206329, measured 602.205753 (1.0 ppm)

Synthesis of tert-butylN-[2-[[2-[4-[(2Z)-2-[1-difluoroboranyl-3-(4-methoxyphenyl)-5-phenyl-pyrrol-2-yl]imino-5-phenyl-pyrrol-3-yl]phenoxy]acetyl]amino]ethyl]carbamate (10)

In a flask under argon are dissolved 0.080 g of 9 (0.13 mmol, 1 eq.), 0.070 ml of DIPEA (Sigma) (0.40 mmol, 3 eq.) and 0.076 g of HBTU (Sigma) (0.20 mmol, 1.5 eq.) In 5 mL of dichloromethane and 1 mL of distilled acetonitrile. The reaction is stirred for 15 minutes and then 0.032 g of Boc-ethylene diamine (0.20 mmol, 1.5 eq.) dissolved in 2 mL of anhydrous dichloromethane are added. The reaction is stirred 1:30. Then, the solution is extracted with dichloromethane and washed successively with 1M KHSO$_4$, NaHCO$_3$ sat. and NaCl sat. The organic phases are combined and dried over MgSO$_4$, filtered and concentrated in vacuo. The residue is then purified by chromatography on silica with a PE/EA mixture giving 0.069 g of a deep blue solid with metallic reflections (0.093 mmol, 71%).

$^1$H NMR (250 MHz, Chloroform-d) δ 8.10-7.98 (m, 8H), 7.51-7.44 (m, 6H), 7.02 (dd, J=9.0, 8), 1 Hz, 4H), 6.94 (d, J=1.1 Hz, 2H), 4.88 (s, 1H), 4.58 (s, 2H), 3.92 (s, 3H), 3.50 (q, J=5.6 Hz, 2H), 3.35 (dd, J=12.1, 6.0 Hz, 2H), 2.80 (s, 3H), 1.43 (s, 9H).

$^{13}$C NMR (101 MHz, CDCl$_3$) δ 131.13, 131.08, 130.96, 130.79, 129.66, 128.69, 125.36, 117.98, 117.94, 115.03, 114.2, 67.41, 55.65, 38.76, 28.49.

HRMS: [M+H]$^+$ C$_{24}$H$_{41}$BF$_2$N$_5$O$_5$ m/z calculated 744.317054, measured 744316900 (0.2 ppm).

1.2. Preparation of 2-[4-[(2Z)-2-[5-[4-[4-(tert-butoxycarbonylamino)) Butoxy]phenyl]-1-difluoroboranyl-3-phenyl-pyrrol-2-yl]imino-5-phenyl-pyrrol-3-yl]phenoxy]methylacetate (19)

This antenna (19) is obtained according to the reaction scheme below:

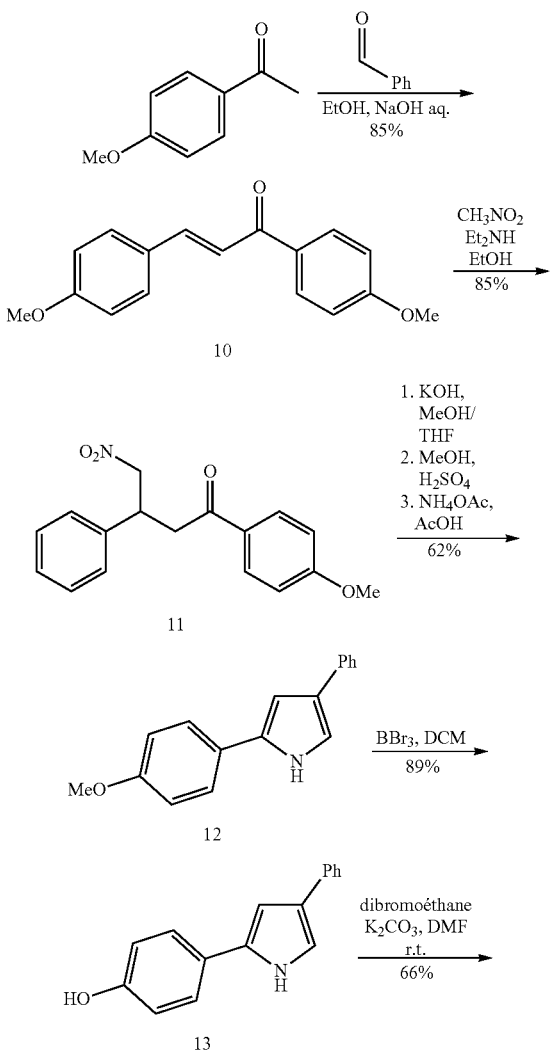

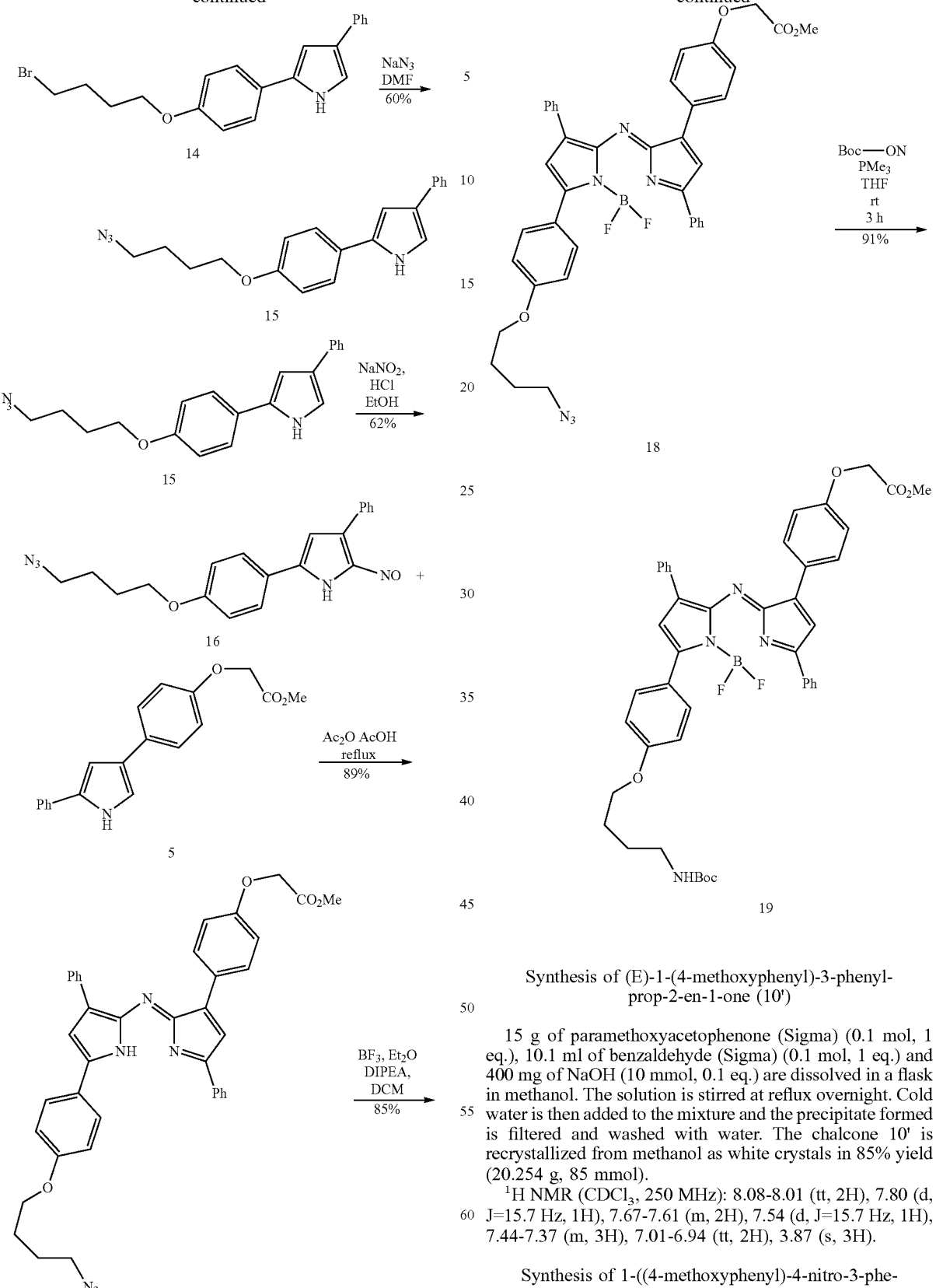

Synthesis of (E)-1-(4-methoxyphenyl)-3-phenyl-prop-2-en-1-one (10')

15 g of paramethoxyacetophenone (Sigma) (0.1 mol, 1 eq.), 10.1 ml of benzaldehyde (Sigma) (0.1 mol, 1 eq.) and 400 mg of NaOH (10 mmol, 0.1 eq.) are dissolved in a flask in methanol. The solution is stirred at reflux overnight. Cold water is then added to the mixture and the precipitate formed is filtered and washed with water. The chalcone 10' is recrystallized from methanol as white crystals in 85% yield (20.254 g, 85 mmol).

$^1$H NMR (CDCl$_3$, 250 MHz): 8.08-8.01 (tt, 2H), 7.80 (d, J=15.7 Hz, 1H), 7.67-7.61 (m, 2H), 7.54 (d, J=15.7 Hz, 1H), 7.44-7.37 (m, 3H), 7.01-6.94 (tt, 2H), 3.87 (s, 3H).

Synthesis of 1-((4-methoxyphenyl)-4-nitro-3-phenyl-butan-1-one (11)

This compound is synthesized by applying the procedure described for the preparation of compound 2.

Mass obtained: 3.205 g; 10.71 mmol
Yield 85%.
$^1$H NMR (CDCl$_3$, 400 MHz): 7.88-7.86 (d, 2H), 7.31-7.21 (m, 5H), 6.90-6.88 (d, 2H), 4.80 (ddd, J=12.6 Hz, 6.4 Hz, 1.3 Hz, 1H), 4.65 (ddd, J=12.6 Hz, 8.3 Hz, 1.3 Hz), 4.18. (p, J=7.1 Hz, 1H), 3.82 (s, 3H), 3.42-3.29 (m, 2H).
$^{13}$C NMR (CDCl$_3$, 101 MHz): 195.39, 163.88, 139.39, 130.39, 129.52, 129.06, 127.83, 127.51, 113.93, 79.68, 55.56, 41.22, 39.49.

Synthesis of
2-(4-methoxyphenyl)-4-phenyl-1H-pyrrole (12)

This compound is synthesized by applying the procedure described for the preparation of compound 3.
Mass obtained: 1.917 g; 7.69 mmol
Yield: 62%
$^1$H NMR (CDCl$_3$, 250 MHz): 8.37 (s, 1H), 7.57 (dd, J=8.4 Hz, 1.3 Hz, 2H), 7.48-7.42 (m, 2H), 7.36 (t, J=7.5 Hz, 3H), 7.23-7.16 (m, 1H), 7.11 (dd, J=2.6 Hz, 1.7 Hz, 1H)), 6.98-6.91 (m, 2H), 6.71 (dd, J=2.7 Hz, 1.7 Hz, 1H), 3.84 (s, 3H).
$^{13}$C NMR (CDCl$_3$, 63 MHz): 158.63, 135.79, 133.27, 128.77, 126.64, 125.79, 125.73, 125.46, 125.31, 115.00, 114, 55, 103.14, 55.51.

Synthesis of 4-(4-phenyl-1H-pyrrol-2-yl) phenol
(13)

This compound is synthesized by applying the procedure described for the preparation of compound 4.
Mass obtained: 180 mg, 0.77 mmol
Yield: 89%
Mp: >300° C.
HRMS: [M+H]$^+$: 236.1070.
IR (cm$^{-1}$): υ=3215, 1495, 1249, 1171, 1101, 832, 763, 696
$^1$H NMR (Acetone-d$_6$, 250 MHz): 10.41 (s, 1H), 8.29 (s, 1H), 7.62-7.58 (m, 2H), 7.55-7.51 (m, 2H), 7.33-7.27 (m, 2H), 7.22 (dd, J=2.8 Hz, 1.7 Hz, 1H), 7.15-7.08 (m, 1H), 6.89-6.85 (m, 2H), 6.77 (dd, J=2.8 Hz, 1.8 Hz, 1H).

Synthesis of 2-[4-(4-bromobutoxy)phenyl]-4-phenyl-1H-pyrrole (14)

0.450 g of 13 (1.91 mmol, 1 eq.), 0.794 g of K$_2$CO$_3$ (5.74 mmol, 3 eq.) and 0.69 ml of 1,4-dibromobutane (5 g) are dissolved in a flask at room temperature. 74 mmol, 3 eq.) in DMF. The reaction is stirred vigorously at room temperature overnight. The next day, water is added to the reaction and the mixture is extracted with diethyl ether, the organic phase is washed 3 times with sat. NaCl and the aqueous phases are re-extracted with diethyl ether. The organic phases are combined, dried over MgSO$_4$, filtered and concentrated in vacuo. The residue is dissolved in a minimum of dichloromethane, and the product is precipitated by addition of petroleum ether, filtered through Buchner and washed with petroleum ether giving 0.466 g of 14 (1.26 mmol, 66%) form of a white powder.
Mp 160-162° C.
HRMS: [M($^{79}$Br)+H]$^+$: 371, 1813, [M($^{81}$Br)+H]$^+$: 373.0814, [M+H]$^+$: 372.0781.
IR (cm$^{-1}$): υ=3395, 1497, 1247, 830, 802, 751, 692.
$^1$H NMR (DMSO-d$_6$, 250 MHz): 11.28 (s, 1H), 7.61-7.57 (m, 4H), 7.34-7.31 (d, 2H), 7.28-7.25 (dd, 1H), 7.14-7.07 (tt, 1H), 6.95 (d, J=2.8 Hz, 2H), 6.80 (dd, J=2.7 Hz, 1.7 Hz, 1H), 4.02 (t, J=6.1 Hz, 2H), 3.62 (t, J=6.5 Hz, 2H), 2.01-1.94 (m, 2H), 1.88-1.81 (m, 2H).

$^{13}$C NMR (DMSO-d$_6$, 63 MHz): 156.82, 135.86, 132.27, 128.48, 125.59, 124.88, 124.76, 124.49, 124.33, 115.71, 114.71, 101.94, 66.59, 34.86, 29.11, 27.42.

Synthesis of 2-[4-(4-azidobutoxy)phenyl]-4-phenyl-1H-pyrrole (15)

0.450 g of 14 (1.22 mmol, 1 eq.) and 0.395 g of sodium azide (Sigma) (6.08 mmol, 5 eq.) in DMF are dissolved in a flask. The reaction is stirred at room temperature overnight. The mixture is dissolved in dichloromethane and washed several times with sat. NaCl. The organic phase is dried over MgSO$_4$, filtered and concentrated in vacuo. After dilution with a minimum of dichloromethane, the product 15 is precipitated by the addition of petroleum ether. The solid is filtered through Buchner and 243 mg of 15 (0.73 mmol, 60%) is obtained as a white powder.
Mp: 177-180° C.
HRMS: [M+H]$^+$: 333.1707.
IR (cm$^{-1}$): υ=3394, 2948, 2875, 2080, 1496, 1246, 831, 752, 692.
1H NMR (CDCl$_3$, 250 MHz): 8.38 (s, 1H), 7.59-7.55 (m, 2H), 7.45-7.39 (m, 2H), 7.37-7.33 (m, 2H), 7.23-7.17 (m, 1H), 7.10-7.08 (m, 1H), 6.94-6.88 (m, 2H), 6.72 (dd, J=2.6 Hz, 1.5 Hz, 1H), 4.01 (t, J=5.8 Hz, 2H), 3.38 (t, J=6.3 Hz, 2H), 1.89-1.80 (m, 4H)
$^{13}$C NMR (CDCl$_3$, 63 MHz): 157.86, 135.76, 133.21, 128.77, 126.57, 125.89, 125.77, 125.41, 125.27, 116.09, 115.09, 103.09, 67.41, 51.34, 26.66, 25.90.

Synthesis of 5-[4-(4-azidobutoxy)phenyl]-2-nitroso-3-phenyl-1H-pyrrole (16)

This compound (ocher-golden powder) is synthesized by applying the procedure described for the preparation of compound 6.
Mass obtained: 67 mg, 0.186 mmol
Yield: 62%
Melting point: 125-126° C.
HRMS: [M+H]$^+$: 362.11612.
IR (cm$^{-1}$): υ=3280, 2918, 2850, 2092, 1603, 1360, 1258, 1164, 1038, 828, 768, 695, 668.
$^1$H NMR (CDCl$_3$, 250 MHz): 8.14-8.11 (m, 2H), 7.84 (d, J=8.4 Hz, 2H), 7.46 (dd, J=5.2 Hz), 1.9 Hz, 3H), 7.15 (s, 1H), 6.99 (d, J=8.2 Hz, 2H), 4.06 (t, J=5.8 Hz, 2H), 3.39 (t, J=6.4 Hz, 2H), 1.93-1.78 (m, 4H).
$^{13}$C NMR (CDCl$_3$, 63 MHz): 163.72, 162.05, 142.84, 131.91, 129.71, 129.57, 129.29, 128.93, 122.19, 115.47, 115.03, 67.67, 51.27, 26.53, 25.82.

Synthesis of 2-[4-[(2Z)-2-[[5-[4-(4-azidobutoxy)phenyl]-3-phenyl-1H-pyrrol-2-yl]imino]-5-phenyl-pyrrol3-yl]phenoxy]methyl acetate (17)

This compound (intense blue powder) is synthesized by applying the procedure described for the preparation of compound 7.
Mass obtained: 0.080 g, 0.123 mmol
Yield: 89%.
Mp: 150-152° C.
HRMS: [M+H]$^+$: 651.2717.
IR (cm$^{-1}$): υ=2094, 1759, 1600, 1496, 1241, 1166, 903, 806, 764, 694, 675.
$^1$H NMR (CDCl$_3$, 400 MHz): 8.00 (d, J=7.8 Hz, 4H), 7.92 (d, J=8.3 Hz, 2H), 7.80 (d, J=7), 6 Hz, 2H), 7.48 (t, J=7.5 Hz, 2H), 7.39 (dd, J=12.8 Hz, 6.9 Hz, 4H), 7.17 (s, 1H), 6.99 (d, 3H), 6.93 (d, J=8.4 Hz, 2H), 4.69 (s, 2H), 4.06 (t, J=6.1 Hz, 2H), 3.85 (s, 3H), 3.40 (t, J=6.6 Hz, 2H), 1.91 (dt, J=11.4 Hz, 6.1 Hz, 2H), 1.82 (p, J=6.8 Hz, 2H).

$^{13}$C NMR (CDCl$_3$, 101 MHz): 169.49, 161.27, 160.76, 157.61, 153.83, 148.27, 145.30, 145.27, 138.66, 133.76, 131.94, 130.36, 129.28, 129.22, 129.00, 128.32, 128.22, 128.15, 125.91, 125.50, 117.43, 115.16, 114.52, 111.16, 67.56, 65.53, 52.45, 51.32, 26.61, 25.87.

Synthesis of 2-[4-[(2Z)-2-[5-[4-(4-azidobutoxy) phenyl]-1-difluoroboranyl-3-phenylpyrrol-2-yl] imino-5-phenylpyrrol3-yl]phenoxy]methylacetate (18)

This compound (intense green solid of metallic appearance) is synthesized by applying the procedure described for the preparation of compound 8.

Mass obtained: 0.065 g, 0.093 mmol

Yield: 85%

$^1$H NMR (400 MHz, Acetone-d$_6$): δ 8.27-8.19 (m, 6H), 8.16-8.11 (m, 2H), 7.60-7.46 (m, 7H), 7.29 (s, 1H), 7.14-7.08 (m, 4H), 4.87 (s, 2H), 4.24-4.17 (m, 2H), 3.78 (d, J=2.1 Hz, 3H), 3.47 (t, J=6.5 Hz, 2H), 1.98-1.89 (m, 2H), 1.83 (q, J=7, 4 Hz, 2H).

$^{13}$C NMR (101 MHz, Acetone): δ 133.16, 131.74, 131.33, 130.48, 130.43, 130.29, 129.60, 129.34, 118.67, 115.76, 115.65, 68.49, 65.69, 52.28, 51.76, 27.13, 26.32.

HRMS: [M+H]$^+$ C$_{39}$H$_{34}$BF$_2$N$_6$O$_4$ m/z calculated 699.270390; measured 699.270354 (0.1 ppm)

Synthesis of 2-[4-[(2Z)-2-[5-[4-[4-(tert-butoxycarbonylamino) butoxy]phenyl]-1-difluoroboranyl-3-phenyl-pyrrol-2-yl]imino-5-phenyl-pyrrol-3-yl]phenoxy]methylacetate (19)

In a flask under argon at room temperature are dissolved 0.061 g of 18 (0.087 mmol, 1 eq.) and 0.024 g Boc-ON (Sigma) (0.096 g, 1.1 eq.) in anhydrous THF. To this solution are added 0.096 ml of a 1M solution of trimethylphosphine in toluene (0.096 mmol, 1.1 eq.). The solution is stirred overnight at room temperature. The next day, the solution is checked by TLC and if the starting material is still visible, 1 eq. is added. additional PMe3 and Boc-ON to complete the reaction in one hour. The solution is then washed with sat. NaCl. and extracted with dichloromethane. The organic phase is dried over MgSO$_4$, filtered and concentrated in vacuo. The residue is purified by chromatography on silica (PE/EA) and 0.061 g of 19 (0.079 mmol, 91%) are obtained in the form of an iridescent dark green solid.

$^1$H NMR (400 MHz, Acetone-d$_6$) δ 8.26-8.17 (m, 6H), 8.15-8.09 (m, 2H), 7.52 (td, J=9.6, 8), 9.4.8 Hz, 7H), 7.25 (s, 1H), 7.11-7.05 (m, 4H), 6.00 (s, 1H), 4.85 (s, 2H), 4.16 (dt, J=6.6, 3.4 Hz, 2H), 3.78 (s, 3H), 3.17 (td, J=7.6, 3.8 Hz, 2H), 1.84 (q, J=7.1 Hz, 2H), 1.69 (p, J=7.4 Hz, 2H), 1.41 (s, 9H).

$^{13}$C NMR (101 MHz, acetone) δ 169.64, 163.11, 160.51, 160.29, 158.35, 156.72, 146.61, 145.53, 144.69, 143.18, 133.12, 133.07, 133.04, 131.70, 131.27, 130.44, 130.41, 130.37, 130.26, 129.55, 129.31, 126.86, 124.28, 120.79, 118.57, 115.71, 115.62, 78.39, 68.77, 65.66, 52.28, 41.83, 40.75, 28.68, 27.43, 27.21, 24.44.

HRMS: [M+H]$^+$ C$_{42}$H$_{41}$BF$_2$N$_5$O$_5$ calculated 744.317054, measured 744.316900 (0.2 ppm).

2. Preparation of the Compounds (C)

General Coupling Procedure

In a flask under argon are added TTHA (TCI Chemicals) (10 eq. if coupled with an anthraquinone antenna, 3 eq. if coupled with an azabodipy antenna) in distilled acetonitrile/triethylamine distilled (2/1). The solution is stirred at reflux for 2 h until the TTHA is completely dissolved. In a second flask, 1 equivalent of a compound "antenna-Y-A$_2$-NHBoc" is deprotected in a mixture of dichloromethane/TFA (1/1) for 30 minutes at room temperature. During this time, the reflux of the TTHA solution is stopped and once the solution at room temperature, the flask is immersed in an ice bath and 0.9 equivalents of HBTU/eq. TTHA dissolved in a few mL of acetonitrile is added dropwise to the solution. This solution is activated for 15 min. Meanwhile, the DCM/TFA solution is evaporated under vacuum and the residue is triturated with diethyl ether to remove excess TFA. The supernatant is removed with the pasteur pipette and the TFA salt of the "antenna-Y-A$_2$-NH$^{3+}$" compound is dried under vacuum. This salt is then dissolved in a few mL of acetonitrile and a few drops of triethylamine. This mixture is then added dropwise to the activated TTHA solution. The reaction is allowed to warm to room temperature and stirred overnight. The next day, the reaction is stopped by adding distilled water. Washing is carried out with ethyl acetate and the product is extracted with distilled water. The aqueous phases are collected, concentrated under vacuum and the residue is then lyophilized overnight. Subsequently, the residue is purified by reverse phase chromatography with a water/MeOH gradient and optionally 0.1% TFA. The collected fractions may then be dissolved in a water/MeOH/triethylamine mixture and an ion exchange resin (IRA-400 (Cl)) may be made to recover the TTHA-A$_2$-Y-antenna conjugate in its acid form. with elution MeOH/water/formic acid.

Synthesis of L1: 3-(2-((2-((4-((2-aminoethyl) amino)-5,8-di hydroxy-9,10-dioxo-9,10-dihydroanthracen-1-yl)aminoacid)ethyl)amino)-2-oxoethyl)-6, 9,12-tris(carboxymethyl)-3,6,9,12-tétraazatétradécane-1,14-dioic Synthesized according to the general procedure of coupling from anthraquinone 1,4-Bis[Boc-aminoethylamino]-5, 8-dihydroxyanthracene-9,10-dione (as described in the article by Sylvain Routier, Nicole Cotelle, Jean-Pierre Catteau, Jean-Luc Bernier, Michael J. Waring, Jean-Francois Riou and Christian Bailly, Bioorganic & Medicinal Chemistry, Vol 4, No. 8, pp 1185-1196, 1996)

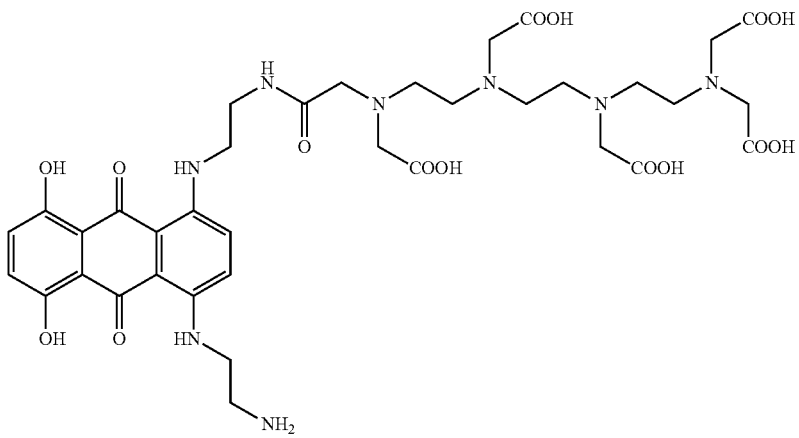 [SMILES: NCCNc1ccc(NCCNC(=O)CN(CCN(CCN(CCN(CC(=O)O)CC(=O)O)CC(=O)O)CC(=O)O)CC(=O)O)c2c1C(=O)c1c(O)ccc(O)c1C2=O]

Yield: 60%, HRMS (ESI) for $C_{36}H_{48}N_8O_{15}$ calculated 832.3239, [M+H]$^+$: 833, 3301 $C_{36}H_{49}N_8O_{15}$ (−1.3 ppm), [M+2H]$^{2+}$ 417, 1697 $C_{36}H_{50}N_8O_{15}$ (−1.0 ppm).

$^1$H NMR (250 MHz, Deuterium Oxide) δ 8.30 (s, 2H), 6.68 (m, 2H) 4.00-3.80 (m, 4H), 3.70-3.25 (m, 30H).

Synthesis of 3,6,9-tris(carboxymethyl)-12-(2-((2-((4-hydroxy-9,10-dioxo-9,10-dihydroanthracen-1-yl)amino)ethylacid)amino)-2-oxoethyl)-3,6,9,12-tétraazatétradécane-1,14-dioic Synthesized according to the general procedure of coupling from anthraquinone 1-[(Boc-aminoethyl)amino]-4-hydroxyanthracene-9,10-dione (as described in the article by Sylvain Routier, Nicole Cotelle, Jean-Pierre Catteau, Jean-Luc Bernier, Michael J. Waring, Jean-Francois Riou and Christian Bailly, Bioorganic & Medicinal Chemistry, Vol 4, No. 8, pp 1185-1196, 1996).

$^1$H NMR (250 MHz, Methanol-d$_4$) δ 8.29-8.16 (m, 2H), 7.86-7.69 (m, 2H), 7.45 (d, J=9.6 Hz, 1H), 7.21 (d, J=9.5 Hz, 1H), 3.85-3.70 (m, 3H), 3.58 (m, 3H), 3.46 (m, 2H), 3.20 (m, 14H).

$^{13}$C NMR (63 MHz, MeOD) δ 188.55, 183.08, 170.80, 157.72, 136.49, 135.39, 133.82, 129.80, 127.77, 127.13, 125.89, 118.16, 114.55, 109.69, 68.85, 42.57, 30.68, 26.48, 9.16.

Synthesis of 2-[2-[2-[bis(carboxymethyl)amino]ethyl-(carboxymethyl)amino]ethyl-[2-[carboxymethyl-[2-[2-[[2-[4-[(2Z)-2-[1-difluoroboranyl-3-(4-methoxyphenyl)-5-phenyl-pyrrol-2-yl]imino-5-phenyl-pyrrol-3-yl]phenoxy]acetyl]amino]ethylamino]-2-oxoethyl]amino]ethyl]amino]acetic Synthesized according to the general procedure of coupling from azabodipy 10 (as described in the article by Sylvain Routier, Nicole Cotelle, Jean-Pierre Catteau, Jean-Luc Bernier, Michael J. Waring, Jean-Francois Riou and Christian Bailly Bioorganic & Medicinal Chemistry, Vol 4, No. 8, pp 1185-1196, 1996).

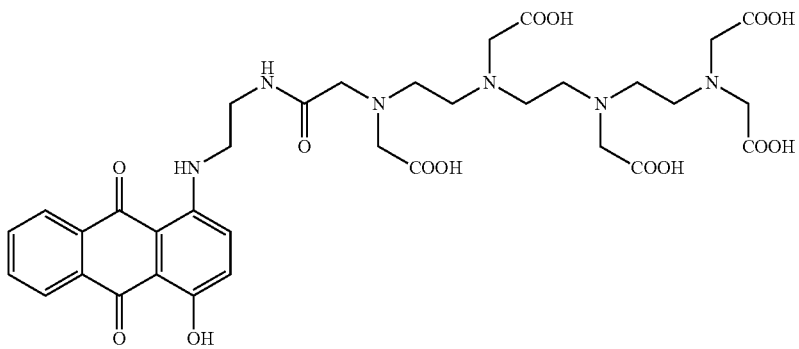 [SMILES: O=C(O)CN(CCN(CCN(CC(=O)O)CC(=O)NCCNc1ccc(O)c2c1C(=O)c1ccccc1C2=O)CC(=O)O)CCN(CC(=O)O)CC(=O)O]

Yield: 60%. HRMS (ESI) for C34H42N6O14 calculated 758.2759, [M+H]$^+$: 759, 283160 $C_{34}H_{43}N_6O_{14}$ 0 ppm), [M+2H]$^{2+}$ 380, 145794 $C_{34}H_{44}N_6O_{14}$ (1.5 ppm).

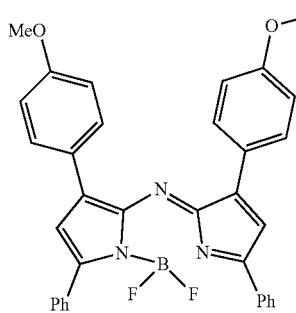
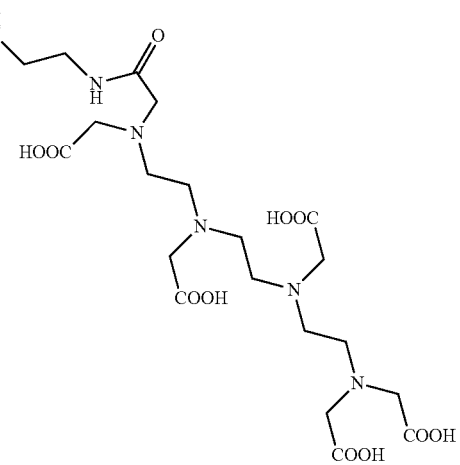

Yield: 70%

$^1$H NMR (250 MHz, methanol-$d_4$) δ 8.19-7.99 (m, 8H), 7.67-7.45 (m, 6H), 7.15 (m, 4H), 7.06 (s, 1H), 7.02 (s, 1H), 4.62 (s, 2H), 3.90-3.80 (m, 15H), 3.50-3.35 (m, 16H).

Synthesis of 2-[2-[2-[bis(carboxymethyl)amino]ethyl-(carboxymethyl)amino]ethyl-[2-[carboxymethyl-[2-[4-[4-[1-difluoroboranyl]-5-[(Z)-[3-[4-(2-methoxy-2-oxo-ethoxy)phenyl]-5-phenyl-pyrrol-2-ylidene]amino]-4-phenyl-pyrrol-2-yl]phenoxy]butylamino]-2-oxoethyl]amino]ethyl]amino]acetic Synthesized according to the general procedure of coupling from azabodipy 19 (as described in the article by Sylvain Routier, Nicole Cotelle, Jean-Pierre Catteau, Jean-Luc Bernier, Michael J. Waring, Jean-Francois Riou and Christian Bailly Bioorganic & Medicinal Chemistry, Vol 4, No. 8, pp 1185-1196, 1996).

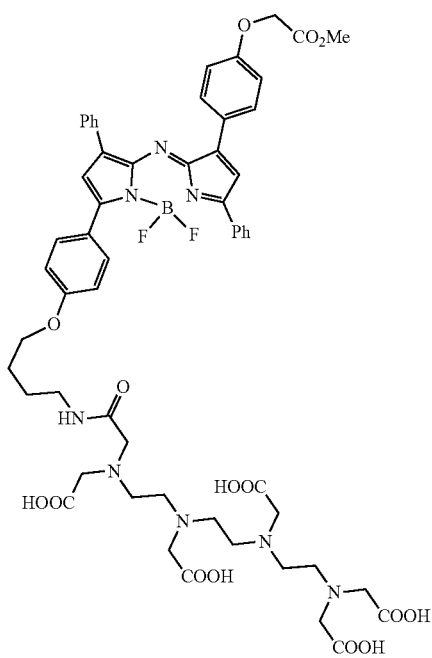 [SMILES: COC(=O)COc1ccc(C2=CC(c3ccccc3)=N/C2=N\c2c(-c3ccccc3)cc(-c3ccc(OCCCCNC(=O)CN(CCN(CCN(CCN(CC(=O)O)CC(=O)O)CC(=O)O)CC(=O)O)CC(=O)O)cc3)n2B(F)F)cc1]

Yield: 75%

$^1$H NMR (250 MHz, MeOD) δ 8.18-8.15 (m, 2H), 7.95-7.9 (m, 3H), 7.86-7.80 (m, 3H), 7.72-7.67 (m, 2H), 7.65-7.58 (m, 7H), 7.50-7.30 (m, 3H), 4.64 (s, 2H), 3.61-3.55 (m, 9H), 3.50-3.40 (m, 16H), 3.30-3.10 (m, 6H), 1.29-1.18 (m, 4H).

Example 2: Synthesis of a Complex According to the Invention

The $Nd^{3+}$ complex was synthesized in situ by the 1:1 mixture of L1 solution (as detailed above), with a solution of neodymium (III) nitrate in HEPES buffer at pH=7.5.

Example 3: Properties of Complexes According to the Invention

1. Photophysical Properties

L1 ligand and $L1Nd^{3+}$ complex (Example 2) both have broad absorption bands which extend over a wavelength range having values as high as 750 nm with maxima centered at ~615 and ~670 nm and molar absorption coefficients up to $5 \cdot 10^3$ $M^{-1}$ $cm^{-1}$. Upon excitation of the low energy absorption bands located on L1 and on the $L1Nd^{3+}$ complex, it is possible to observe broadband emission signals from the chromophore ligand centered at ~690 nm with a shoulder at ~740 nm. The complex $L1Nd^{3+}$, when excited at a wavelength of 650 nm, produces a narrow emission band with a maximum at 1064 nm which is characteristic of the electronic structure of $Nd^{3+}$ resulting from the transition $^4F_{3/2} \rightarrow {}^4I_{11/2}$. The excitation spectra recorded by observing either the ligand emission signal centered at 740 nm or the $Nd^{3+}$ narrow emission signal centered at 1064 nm are superimposed on the absorption spectra indicating that the sensitization of the lanthanide cation is performed using the electronic levels of the chromophore derived from the anthraquinone ligand L1. As a result, ligand L1 and complex $L1Nd^{3+}$ both have excitation and emission wavelengths included in the domain of the biological diagnostic window (FIG. 1).

The quantitative luminescence parameters (luminescence lifetime (i) and luminescence quantum yields centered on L1-($Q_L$) and on $Nd^{3+}$-($Q_{Nd}$)) determined on the $L1Nd^{3+}$ complex are summarized in Table 3.1.

Relatively short life time values T (in the nanosecond range) and low QNd quantum yields have been measured for the near-infrared emission of $Nd^{3+}$ in comparison with the highest corresponding values that have been published to date. (J.-C. G. Bünzli, S. V. Eliseeva, Photophysics of Lanthanoid Coordination Compounds, in: VW-W Yam (Ed.) Comprehensive Inorganic Chemistry II, Elsevier BV, Amsterdam, 2013, pp. 339-398, and J.-C. G. Bünzli, On the design of highly luminescent complex lanthanide, Coordination Chemistry Reviews, 293-294 (2015) 19-47). The analysis of the lifetimes measured on the L1Nd$^{3+}$ complex in H$_2$O and D$_2$O reveals that no water molecule is directly bound to the lanthanide cations, which is a strong indication of the good level of protection that is provided by the TTHA coordination entity.

Figure 3:
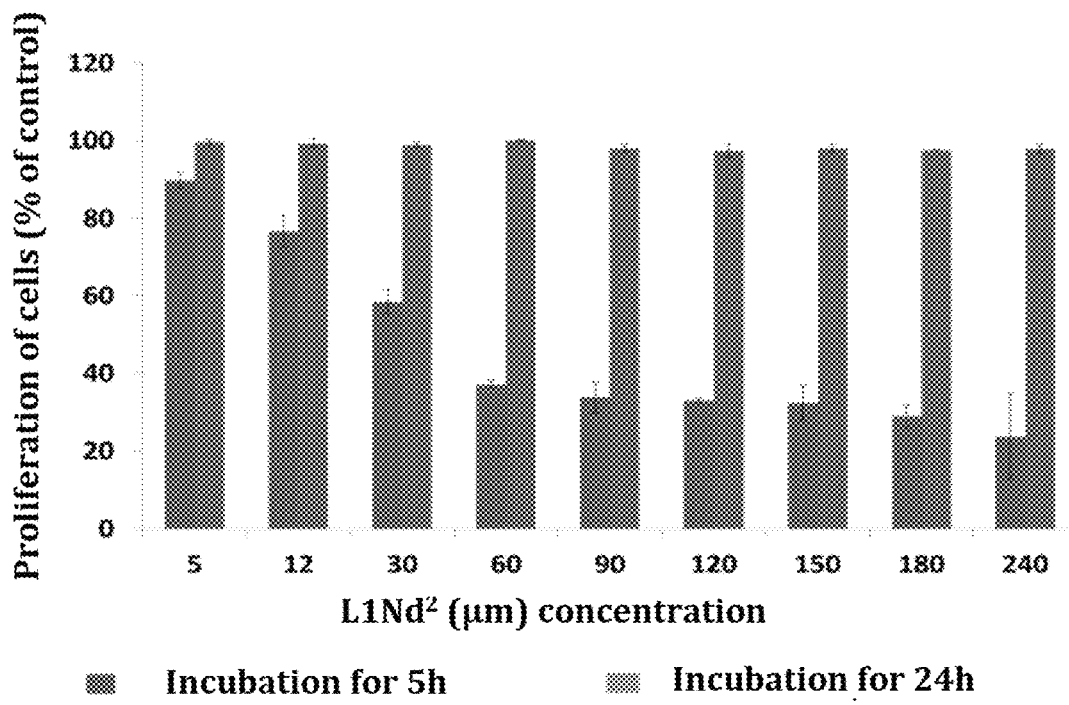
FIG. 3 shows the results of cytotoxicity tests obtained with the aid of the "Alamar Blue" test carried out on HeLa cells incubated with varying concentrations of L1Nd$^{3+}$ complexes for 5 h (left columns) and 24 h (left columns).

The quantum yield of the emission from the ligand is lower by a ratio of 30% for the Nd$^{3+}$ complex relative to the L1 ligand. This result is indicative of the presence of energy transfer between the anthraquinone chromophore and the Nd$^{3+}$ cation. It is important to point out that narrow Nd$^{3+}$ emission band positions are unaffected by microenvironmental changes, which is a major advantage over the "wavelength" indocyanine green commercial fluorophore. of similar excitation (Fernandez-Fernandez, R. Manchanda, T. Lei, D. A. Carvajal, Y. Tang, S. Z. Razza Kazmi, A. J. McGoron, Comparative study of the optical and heat generation properties of IR820 and indocyanine green, Molecular imaging, 11 (2012) 99 and S. Mordon, J. M. Devoisselle, S. Soulie-Begu, T. Desmetter, Indocyanine green: Physicochemical factors affecting its fluorescence in vivo, Microvascular Research, 55 (1998) 146-152).

working concentration of 5 µM corresponding to a cell viability rate of 90% was chosen for the microscopy experiments. Shorter incubation times (5 h) allowed the viability of HeLa cells to be preserved without effects resulting from the presence of the L1Nd$^{3+}$ complex being detectable up to concentrations as high as 240 µM (FIG. 3).

Confocal Microscopy

Figure 4:
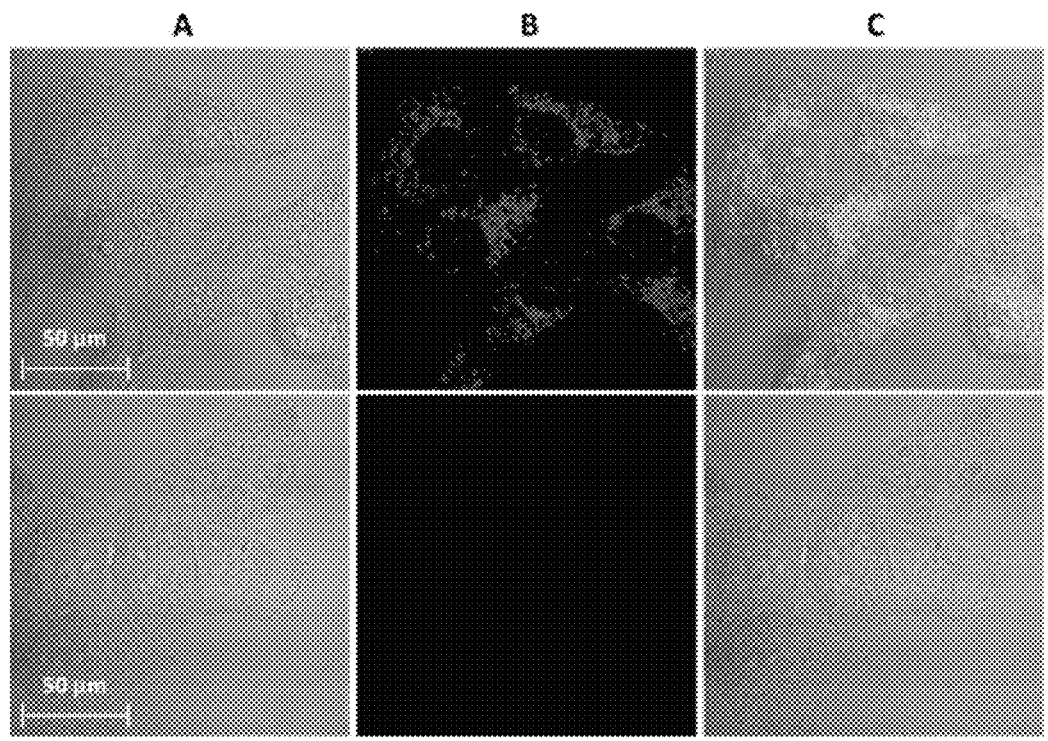
FIG. 4 shows images obtained during confocal microscopy experiments carried out on HeLa cells (top images) incubated with a 5 µM solution of the L1Nd$^{3+}$ complex for 3 h and (bottom images) on control cells which were not incubated with the L1Nd$^{3+}$ complex. (A) Visible transillumination image, (B) Emission centered on L1 ligand ($\lambda_{ex}$: 633 nm, $\lambda_{em}$: 650-750 nm), (C) Result of the fusion of the images. Single shot images selected in the middle of the cell volume (in the kernel plane).

The internalization of the L1Nd$^{3+}$ complex in HeLa live cells was confirmed by confocal microscopy experiments on samples obtained after incubation for 3 h with a 5 µM L1Nd$^{3+}$ solution. When these incubated HeLa cells are observed using a 633 nm laser excitation and selecting optical slices of thicknesses of 1 µm in the vertical plane, the emission from the anthraquinone derivative could be detected on a wavelength range of 650 to 750 nm (FIG. 4). The intracellular distribution of the luminescence signal suggests a localization with lysosomes. The absence of autofluorescence signals for these wavelengths confirms that the imaging performed in the biological diagnostic window significantly improves the signal-to-noise ratio of the measurement and the sensitivity of detection.

Figure 5:
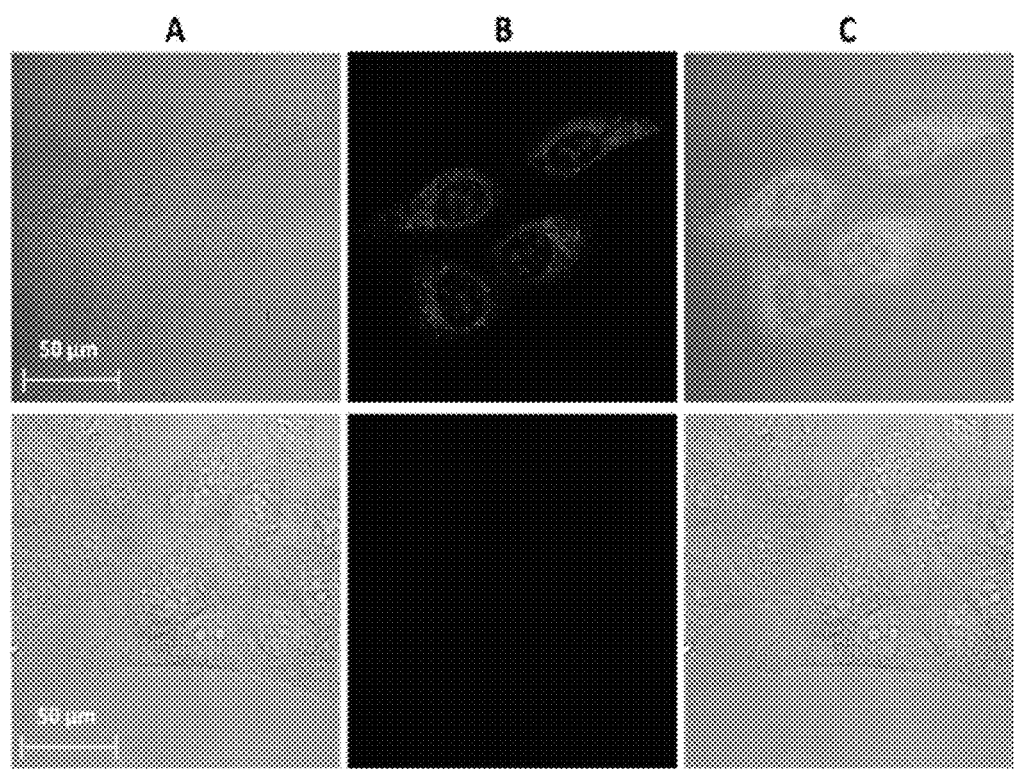
FIG. 5 shows images obtained from confocal microscopy experiments conducted on HeLa cells (top images) incubated with a 50 µM solution in L1Nd$^{3+}$ for 3 h and (bottom images) on control cells which were treated in a similar manner. with the exception of the absence of incubation with the L1Nd$^{3+}$ complex. (A) Visible transillumination, (B) L1 ligand centered emission ($\lambda_{ex}$: 633 nm, $\lambda_{em}$: 650-750 nm), (C) Result of image fusion. Single plane images located in the middle of the cell volume (in the plane of the nucleus).

When HeLa cells were incubated with higher concentrations of L1Nd$^{3+}$ complex (50 µM), the luminescence signal could be detected not only in lysosomes but also in nucleosomes (FIG. 5).

Flow Cytometry

In addition to the confocal microscopy experiments, the internalization of the L1Nd$^{3+}$ complex was quantitatively confirmed by a flow cytometry analysis carried out on a

TABLE 3.1

Photophysical Properties of L1 Ligand L1Nd$^{3+}$ Complex (100 µM, pH = 7.5, measured at room temperature)

| Compound | T (ns) [b] | | | $Q_{Nd}$ (%) [d] | | |
|---|---|---|---|---|---|---|
| | H$_2$O | D$_2$O | q (H$_2$O) [c] | H$_2$O | D$_2$O | $Q_L$(%) [e] |
| L1Nd$^{3+}$ | 148(2) | 389(1) | 0,1 | 1,80(3) ·10$^{-3}$ | 7,9(2) ·10$^{-3}$ | 0,177(8) |
| L1 | — | — | — | — | — | 0,257(5) |

[a] The values of 2σ are indicated in parentheses. Experimental errors: T, ± 2%, Q, ± 10%.
[b] Obtained under excitation at 680 nm.
[c] The number of water molecules coordinated with the lanthanide cation (q) was calculated using the equations:

$$q_{Nd} = 130 \times \left(\frac{1}{\tau_{H2O}} - \frac{1}{\tau_{D2O}}\right) - 0.4$$

The estimated error is ± 0.2 (S. Faulkner, A. Beeby, M.-C. Carrié, A. Dadabhoy, A.M. Kenwright, P.G. Sammes, Time-resolved near-IR luminescence from ytterbium and neodymium complexes of the Lehn cryptand, Inorganic Chemistry Communications, 4 (2001) 187-190).
[d] obtained with an excitation wavelength of 650 nm, partial quantum yield measured for the transition $^4F_{3/2} \rightarrow {^4I_{11/2}}$.
[e] Under excitation at 620 nm, the emission signal was collected on the spectral range of 640-850 nm.

Figure 2:
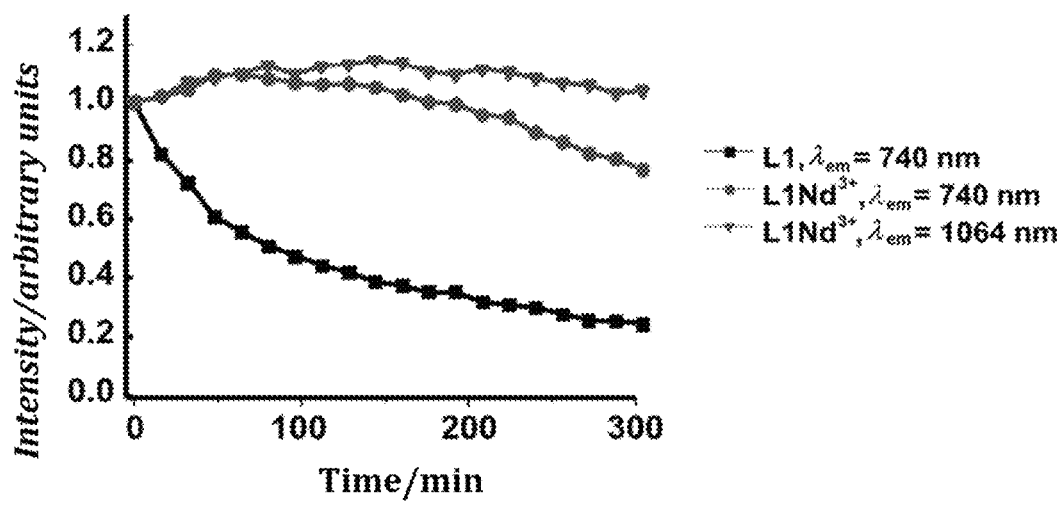
FIG. 2 shows the results of photostability tests obtained on solutions of 100 µM solutions of L1 ligand and L1Nd$^{3+}$ complex in the HEPES buffer (pH=7.5) under continuous illumination at 630 nm at room temperature.

The photostabilities of L1 and L1Nd$^{3+}$ were studied under continuous illumination at 630 nm (FIG. 2). The presence of the lanthanide cation (Nd$^{3+}$) has been shown to significantly improve photostability. Thus, the light intensities emitted from the ligand ($\lambda_{em}$=740 nm) and the lanthanide Nd$^{3+}$ ($\lambda_{em}$=1064 nm) within the complex do not decrease after 3 h of continuous illumination while the emission of the free ligand loses ~70% of its initial intensity under identical experimental conditions. These results can be explained in the first hypothesis by the concentration of the energy coming from the triplet state of L1 in the case of the L1Nd$^{3+}$ complex.

Cytotoxicity Tests

Figure 6:
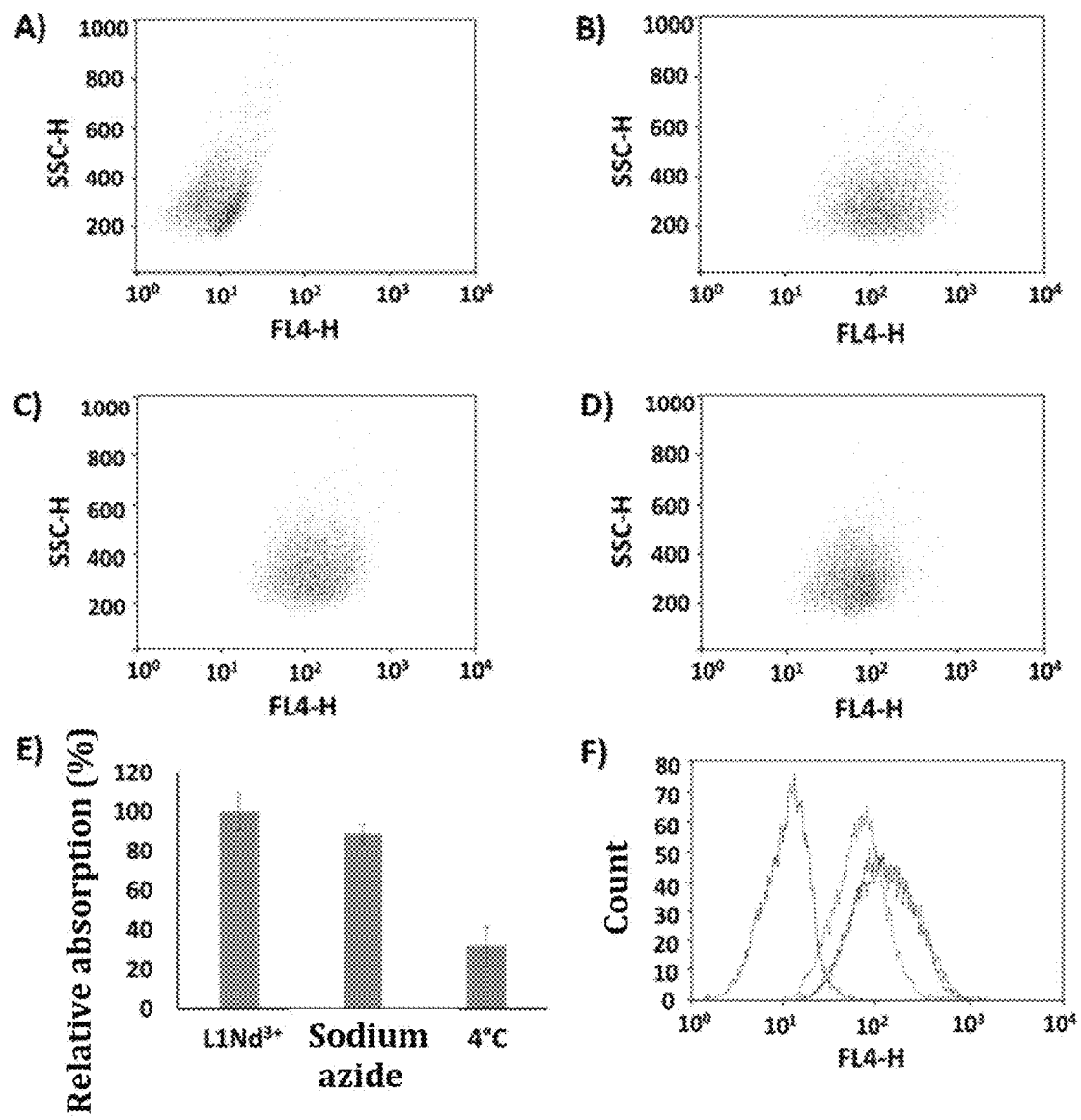
FIG. 6 shows results of flow cytometry experiments. The HeLa cells were observed after 3 h of incubation in the Opti-MEM+2% FBS culture medium: (A) control cells which were treated in a similar manner with the exception of the absence of incubation with the L1Nd$^{3+}$ complex; (B) a 5 µM solution of L1Nd$^{3+}$ complex; (C) a solution containing 5 µM L1Nd$^{3+}$ and 100 mM sodium azide and (D) a solution of 5 µM L1Nd$^{3+}$ at 4° C. The measurement conditions of (C) and (D) imply that the cells were either preincubated with a solution of 100 mM sodium azide or placed at 4° C. for 30 min before being incubated with the solution. of L1Nd$^{3+}$. Dotted diagrams represent the distributions of cells in "2FSC (forward scatter)" and "SSC (side scatter)" mode; (E) Quantification of cellular incorporation of L1Nd$^{3+}$ complex measured under different experimental conditions. In order to facilitate reading of the data, the fluorescence intensity from HeLa cells incubated with the L1Nd$^{3+}$ complex without transport inhibition was normalized at 100% incorporation with an RSD of ±9.38; (F) Histograms corresponding to experimental conditions A, B, C, D.

In order to determine the cytotoxicity of the L1Nd$^{3+}$ complex in living cells, "Alamar Blue" type assays were performed on the HeLa cell line. After 24 hours of incubation with the L1Nd$^{3+}$ complex, we observed a viability rate of 77% at a concentration of 12 µM. For this reason, a sample of 10$^4$ cells under excitation at 633 nm and analyzing the emission from the chromophore derived from anthraquinone located on the chromophore ligand (FIG. 6).

The mechanism of cellular incorporation was analyzed by inhibition of active transports, which are dependent on energy (incubation with sodium azide NaN$_3$) and passive (incubation at 4° C.). Due to the increased stiffness of the membrane during incubation at 4° C., in addition to the inhibition of passive transport, those that are active are also deactivated. The results obtained make it possible to conclude without ambiguity that the L1Nd$^{3+}$ complex is incorporated mainly via a passive transport mechanism since 69±10% of the incubation of L1Nd$^{3+}$ was blocked by incubation at 4° C. whereas 11±5% of L1Nd$^{3+}$ complex were transported by an active process.

Epifluorescence Microscopy

Figure 7:
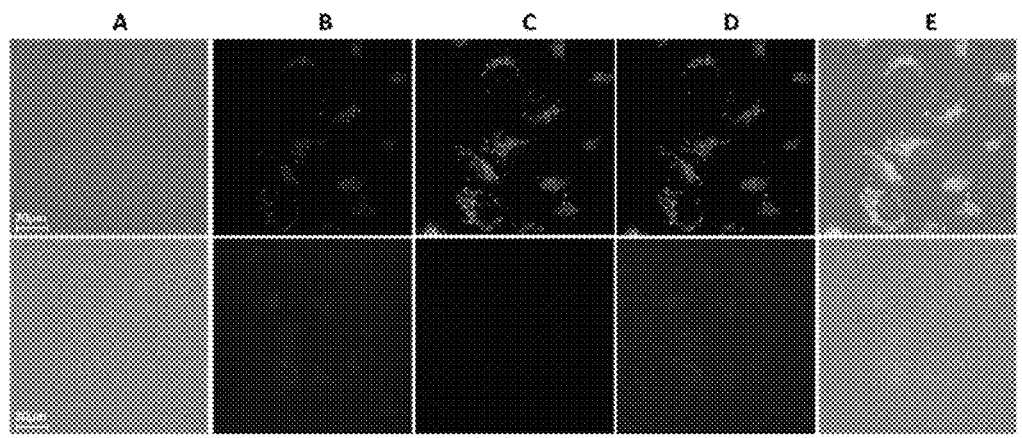
FIG. 7 shows results of epifluorescence microscopy experiments conducted on HeLa cells. Co-localization of the L1Nd$^{3+}$ complex in HeLa cells (high) after incubation for 3 h with a 5 µM solution of L1Nd$^{3+}$ complex and 30 min incubation with a 50 nM solution of "LysoTracker Yellow". (A) Visible Transillumination, (B) "LysoTracker Yellow" Emission ($\lambda_{ex}$: 485 nm filter with 20 nm bandwidth, $\lambda_{em}$: 540 nm filter with 50 nm bandwidth, 800 ms exposure time) (C) L1Nd$^{3+}$ emission in the near-infrared ($\lambda_{ex}$: filter at 655 nm bandwidth 40 nm; $\lambda_{em}$: low cut filter at 805 nm, exposure time of 20 s), (D) image resulting from the combination of the image of the emission of "LysoTracker Yellow" and the image of the emission of Nd$^{3+}$, (E) image resulting from the combination of the fluorescence image of "LysoTracker Yellow", of the emission centered on the Nd$^{3+}$ and visible transillumination. (Bottom) control cells that were similarly treated with the exception of the lack of incubation with the L1Nd$^{3+}$ complex. Objective offering a magnification of 63×.

Despite the low quantum yield of L1Nd$^{3+}$, it was possible to perform near infrared imaging measurements with good sensitivity in Hela cells using this imaging agent. An intense near-infrared signal (selected by means of a low pass filter at 805 nm) could be observed for the L1Nd$^{3+}$ complex in these HeLa cells by exciting L1Nd$^{3+}$ using a conventional excitation source (Xenon lamp, 655 filter). nm with a bandwidth of 40 nm) (FIG. 7C, top). Due to the absence of autofluorescence in the near-infrared and using the same experimental setup for the control cells compared to the cells incubated with the L1Nd$^{3+}$ complex (FIG. 7C, bottom), we confirmed a signal-to-noise ratio and a greatly improved detection sensitivity for fluorescence imaging agents having excitation and emission wavelengths located in the biological diagnostic window.

In the case of the use of the visible commercial probe used for the specific lysosome labeling, the yellow lysotracker, an autofluorescence can be detected being generated by biomolecules since these have a strong absorption and emission in this region (FIG. 7B, bottom). However, the location of the L1Nd$^{3+}$ complex within the lysosomes was confirmed by an epifluorescence microscopy experiment when the yellow lysotracker was located at the same location as the L1Nd$^{3+}$ complex (FIG. 7d, top).

Figure 8:
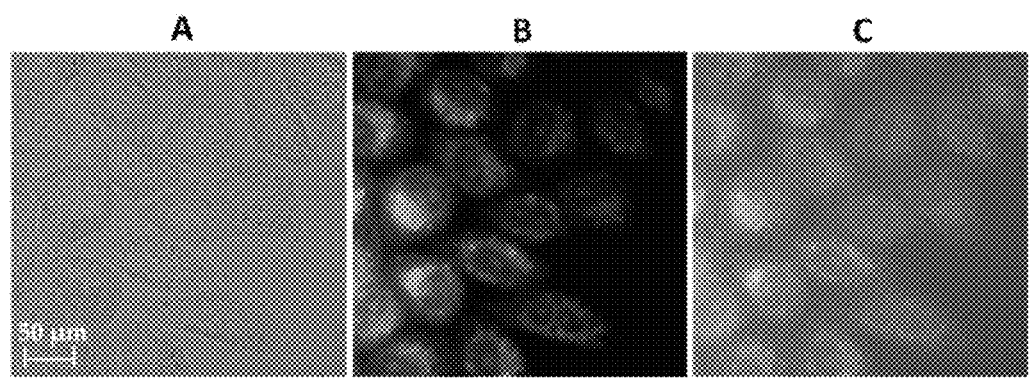
FIG. 8 shows results of epifluorescence microscopy experiments conducted on HeLa cells incubated for 3 h with a 50 µM solution of L1Nd$^{3+}$ complex ($\lambda_{ex}$: 655 nm, 40 nm bandwidth, 805 nm, 15 s of exposure). (A) Visible transillumination, (B) Near-infrared emission ($\lambda_{ex}$: 655 nm, 40 nm bandwidth, λem: 805 nm, 805 nm low cut filter, 20 s exposure time), (C) Combination of images (A) and (B). Magnification objective 63×.

Furthermore, it has been observed with confocal microscopy experiments that when HeLa cells are incubated with a higher concentration of L1Nd$^{3+}$ complex (50 μM), a localization can also be obtained in nucleosomes where an intense near-infrared signal has been detected. could be detected (FIG. 8).

Photobleaching Test Conducted by Epifluorescence Microscopy

Figure 9:
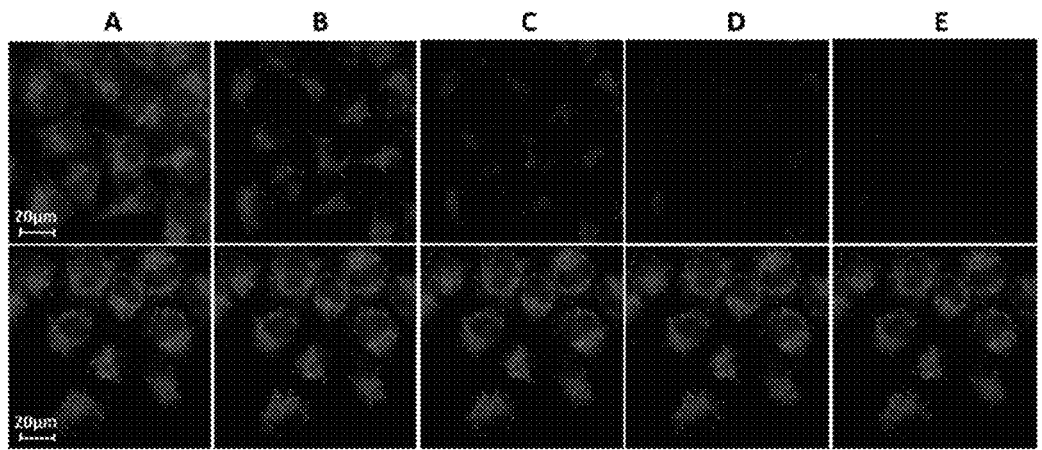
FIG. 9 shows results of photobleaching tests. HeLa cells incubated for 3 h with a 5 µM solution of L1Nd$^{3+}$ complex or 30 min with a 50 nM solution of "LysoTracker Deep Red" after exposure under continuous excitation of light selected by a 655 nm filter of 40 nm bandwidth of different durations (A) 0 s, (B) 20 s, (C) 45 s, (D) 70 s, (E) 95 s. (Top) Emission of "LysoTracker Deep Red" ($\lambda_{ex}$: filter at 655 nm bandwidth of 40 nm, $\lambda_{em}$: filter at 716 nm bandwidth of 40 nm, exposure time of 300 ms). (Bottom) Emission from the anthraquinone chromophore located on the L1Nd³⁺ complex ($\lambda_{ex}$: 655 nm filter with 40 nm bandwidth, $\lambda_{em}$, 716 nm emission with 40 nm bandwidth, 600 ms exposure). Magnification objective 63×.

In order to compare the photostability of the L1Nd$^{3+}$ complex with that of a commercially available reporter, a photobleaching test was performed by comparison with the "LysoTracker Deep Red" followed by epifluorescence microscopy. A significant photobleaching was observed in the case of the "LysoTracker Deep Red" protractor after 20 s of continuous illumination at a light selected by a 655 nm filter (40 nm bandwidth) (FIG. 9, top). On the other hand, the intensity of the emission from anthraquinone in the L1Nd$^{3+}$ complex remained constant during 95 s using the same experimental conditions (selection of the wavelength by a 655 nm filter of 40 nm bandwidth for excitation and 716 nm bandwidth of 40 nm for emission (FIG. 9, bottom).

Figure 10:
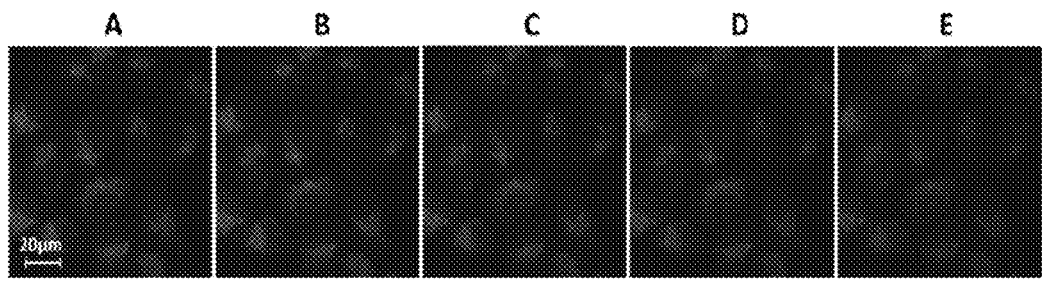
FIG. 10 shows results of photobleaching test experiments. HeLa cells incubated with a 5 μM solution of L1Nd³⁺ for 3 h and then exposed to controlled continuous illumination by means of a 655 nm filter with a 40 nm bandwidth of different durations: (A) 0 s, (B) 120 s, (C) 245 s, (D) 370 s, (E) 495 s. Detection of near-infrared emission ($\lambda_{ex}$: 655 nm filter with 40 nm bandwidth, $\lambda_{em}$: 805 nm low cut filter, 20 s exposure time, 63× magnification objective).

A constant emission signal collected through a low-cut filter (805 nm, FIG. 10) could be observed revealing a very satisfactory photostability was measured up to 495 seconds for the complex L1Nd$^{3+}$ under continuous illumination by means of light selected by a filter at 655 nm bandwidth of 40 nm.

Figure 11:
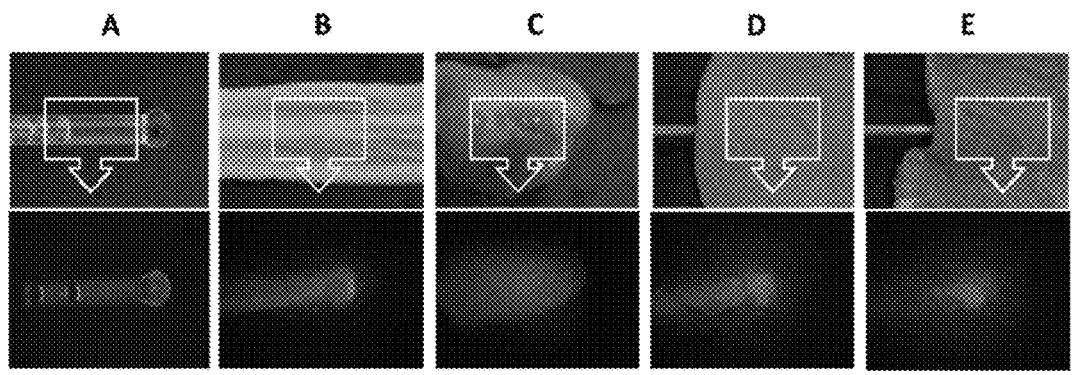
FIG. 11 shows results of near-infrared epifluorescence macroscopy experiments conducted with a 200 μM solution of L1Nd³⁺ placed in a glass capillary (A) and covered with biological tissues of different origins and thicknesses: chicken skin of 0.6 mm (B), 2 mm chicken liver (C), 1.6 mm beef flesh (D), 3 mm pork meat (E). (Top) Visible transillumination and (low) near infrared luminescence images ($\lambda_{ex}$: 685 nm (pulsed laser) $\lambda_{em}$: low pass filter at 785 nm, exposure time 18 s).

Epifluorescence Macroscopy: Detection of Near-Infrared Emission from the L1 Nd$^{3+}$ Complex in/Through Different Biological Samples In order to demonstrate in a complementary manner the advantages of the use of the new imaging agents according to the invention which have excitation and emission wavelengths in the field of the biological diagnostic window and more particularly penetration of photons at greater depths, experiments were conducted on biological tissues of animal origin and varied thicknesses using the following experimental setup: a glass capillary containing a 200 μM solution of L1Nd$^{3+}$ was placed under the different tissue samples (FIG. 11, top) and excited through a pulsed dye laser emitting light of wavelength 685 nm. An intense signal could be collected using a low cut filter at 785 nm (FIG. 11, bottom). This experiment has shown that near-infrared photons from the L1Nd$^{3+}$ complex can be detected through pig tissue with a thickness of 3 mm, chicken liver (2 mm), beef (1.6 mm) or chicken skin (0.6 mm). The tests on tissues of different kinds made it possible to evaluate the tissue absorption differences and the different light diffractions which are two parameters related to the penetration depth of photons and which influence the resolution of the images collected. In addition, a difference in autofluorescence generated according to the nature of the tissues was observed.

Since blood components, in particular hemoglobin, are among the largest light absorbers and the largest emitters of autofluorescence, they can be responsible for a very large loss of signal and can lead to a very large decreased signal-to-noise ratio and measurement sensitivity (A. Taruttis, V. Ntziachristos, Translational Optical Imaging, American Journal of Roentgenology American Roentgen Ray Society, 199 (2012) 263-271). It has been demonstrated here that by using excitation and emission wavelengths included in the biological diagnostic window, it is possible to effectively minimize the undesirable effects of autofluorescence. Thus, it has been possible to detect an intense near infrared signal from L1 Nd$^{3+}$ at a concentration of 200 μM in the blood.

What is claimed is:

1. Complex comprising at least one lanthanide (Ln) and at least one compound (C) comprising a unit of formula (I) below:

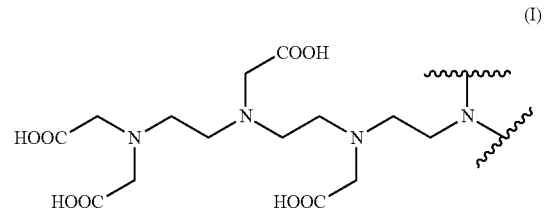

(I)

said unit of formula (I) being connected covalently to at least one antenna which absorbs at a wavelength ranging from 500 nm to 900 nm, said antenna being chosen from the group consisting of: anthraquinones, cyanines, aza-BODIPY, perylenediimides, phenothiazine salts, and their derivatives.

2. Complex according to claim 1, wherein the antenna is connected to the unit of formula (I) covalently via an arm corresponding to the following formula:

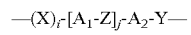

in which:
i is 0 or 1;
j is an integer between 1 and 3;
X is chosen from the functions —NH—NH—CO—, thioester, ester and amide,
$A_1$ and $A_2$ are chosen, independently of one another, from linear or branched (cyclo)alkylene radicals comprising from 1 to 12 carbon atoms;
Z is selected from —O—, —NH—, —S—, amide, ester, triazole, amine, urea, thiourea, imine, oxyme, hydrazone, sulfonamide, carbamate, amidine, phosphoramidate, disulfide and sulfonyl groups; and
Y is selected from —O—, —NH—, —S—, alkylene, amide, ester, triazole, amine, urea, thiourea, imine, oxyme, hydrazone, sulfonamide, carbamate, amidine, phosphoramidate, disulfide and sulfonyl groups.

3. Complex according to claim 1, wherein the compound (C) has the following formula (IV):

(IV)

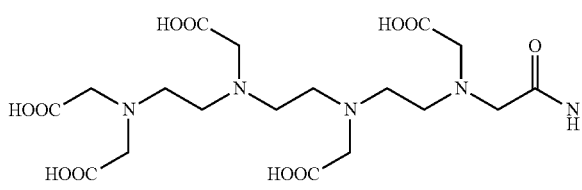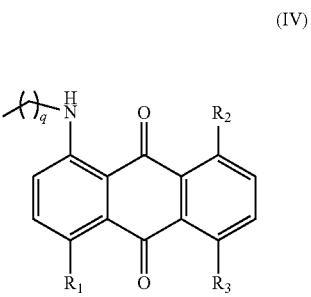

in which:
q being an integer between 1 and 6;
R$_1$ representing:
H;
an —NH—(CH$_2$)$_n$—NH$_2$, group, where n is an integer from 1 to 6;
a group —NH—(CH$_2$)$_n$—R$_α$, n being as defined above and R$_α$ representing a group chosen from: halogens, carboxylic acids, succinimide esters, tetrafluorophenyl esters, acyl azides, anhydrides, acid halides, acrylamides, alcohols, amines, alkynes, cyclooctines, aminooxyacetamides, azides, imidoesters, sulfonate esters, haloacetamides, alkyl halides, sulfonyl halides, hydrazines, hydrazides, isocyanates, isothiocyanates, tetrazines, and maleimides;
a (C$_1$-C$_6$)alkyl group;
a group OR$_a$, R$_a$ representing H or a group (C$_1$-C$_6$) alkyl;
an NR$_a$R$_b$ group, R$_a$ and R$_b$ representing, identical or different, H or a (C$_1$-C$_6$)alkyl group; and
R$_2$ and R$_3$, identical or different, representing:
H;
a (C$_1$-C$_6$)alkyl group;
an OR$_a$ group, R$_a$ being H or a group selected from a (C$_1$-C$_6$)alkyl, (C$_6$-C$_{10}$)aryl and (C$_5$-C$_{10}$)heteroaryl group;
an NH—(CH$_2$)$_n$—R$_α$, group, n and R$_α$ being as defined above; and
an NR$_a$R$_b$ group, R$_a$ and R$_b$, identical or different, representing H or a group selected from the (C$_1$-C$_6$)alkyl, (C$_6$-C$_{10}$)aryl and (C$_5$-C$_{10}$)heteroaryl group.

4. Complex according to claim 1, wherein the compound (C) has the following formula (VI):

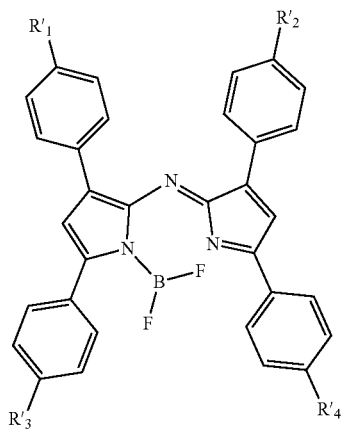

in which:
R'$_1$ is H or is selected from the (C$_1$-C$_6$)alkyl, (C$_1$-C$_6$) alkoxy, and NR$_a$R$_b$ groups, R$_a$ and R$_b$, identical or different, representing H or a (C$_1$-C$_6$)alkyl group;
R'$_2$ is:
an —O-A$_3$-COOR$_a$ group, A$_3$ representing a (C$_1$-C$_6$) alkylene radical and R$_a$ representing H or a (C$_1$-C$_6$)alkyl group;
a group of formula (VI-1) below:

(VI-1)

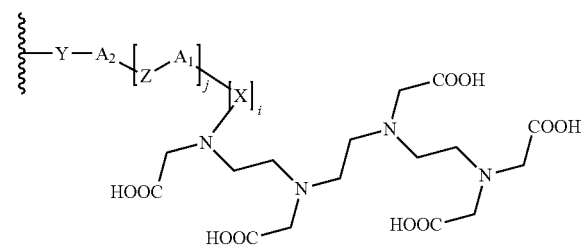

in which:
i is 0 or 1;
j is an integer between 1 and 3;
X is chosen from the functions —NH—NH—CO—, thioester, ester and amide,
A$_1$ and A$_2$ are chosen, independently of one another, from linear or branched (cyclo)alkylene radicals comprising from 1 to 12 carbon atoms;
Z is selected from —O—, —NH—, —S—, amide, ester, triazole, amine, urea, thiourea, imine, oxyme, hydrazone, sulfonamide, carbamate, amidine, phosphoramidate, disulfide and sulfonyl groups;
Y is selected from —O—, —NH—, —S—, alkylene, amide, ester, triazole, amine, urea, thiourea, imine, oxyme, hydrazone, sulfonamide, carbamate, amidine, phosphoramidate, disulfide and sulfonyl groups;
R'$_3$ is H or a group of formula (VI-1) above; and
R'$_4$ is H or is selected from the (C$_1$-C$_6$)alkyl, (C$_1$-C$_6$)alkoxy, and NR$_a$R$_b$ groups, R$_a$ and R$_b$, identical or different, representing H or a (C$_1$-C$_6$)alkyl group;
provided that when R'$_3$=H then R'$_2$ is a group of formula (VI-1) and when R'$_2$=—O-A$_3$-COOR$_a$ then R'$_3$ is a group of formula (VI-1).

5. Complex according to claim 4, wherein the compound (C) has the following formula (VII):

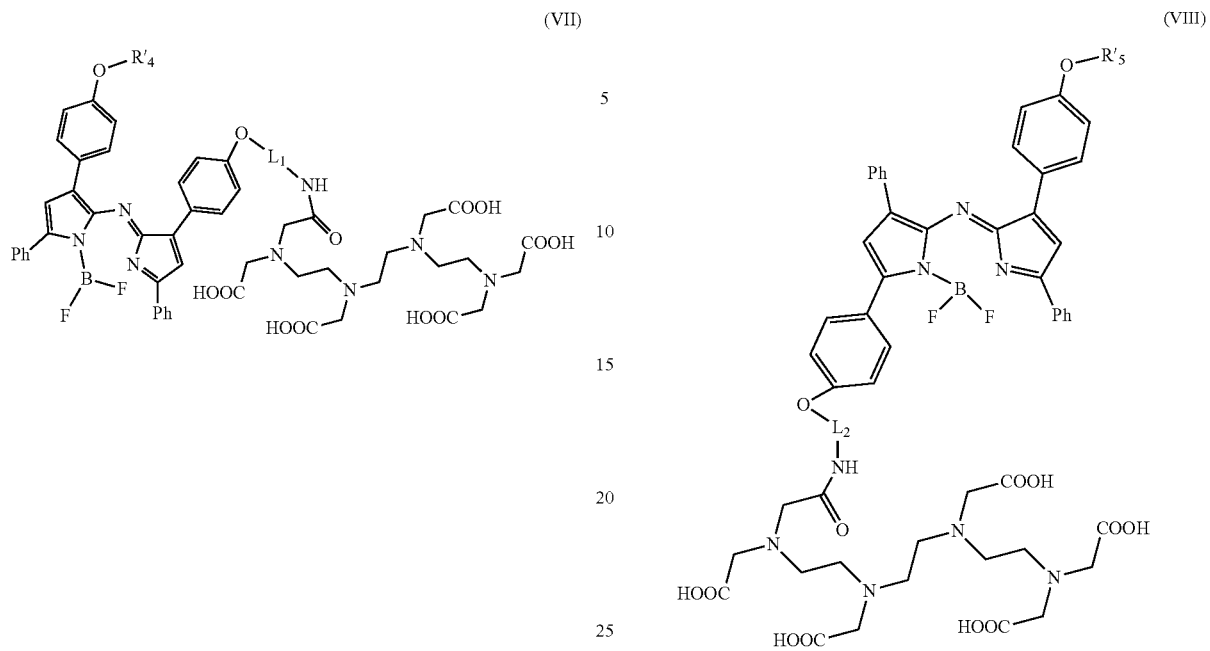

in which:
 L₁ represents a linker chosen from:
  the radicals —$(CH_2)_m$—C(=O)—NH—$(CH_2)_p$—,
  m and p representing an integer between 1 and 4,
 $R'_4$ represents a $(C_1-C_6)$alkyl group.

6. Complex according to claim 4, wherein the compound (C) has the following formula (VIII):

in which:
 L₂ represents a $(C_1-C_6)$alkylene radical, and
 $R'_5$ represents a $(C_1-C_6)$alkyl group, substituted by a COOR$_a$ group, R$_a$ representing H or a $(C_1-C_6)$alkyl group.

7. Complex according to claim 1, wherein the compound (C) has one of the following formulas:

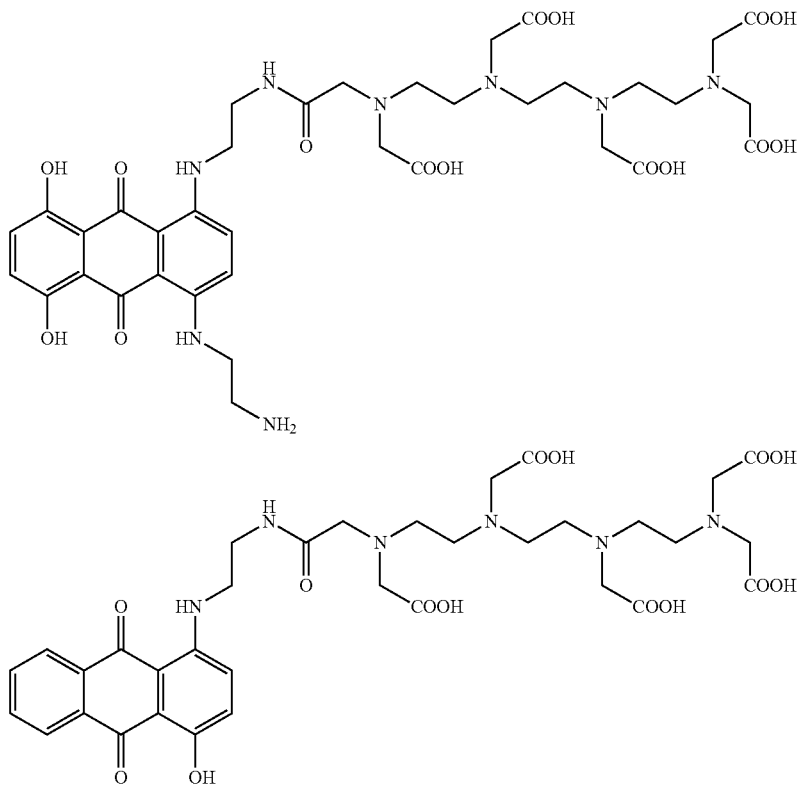

-continued
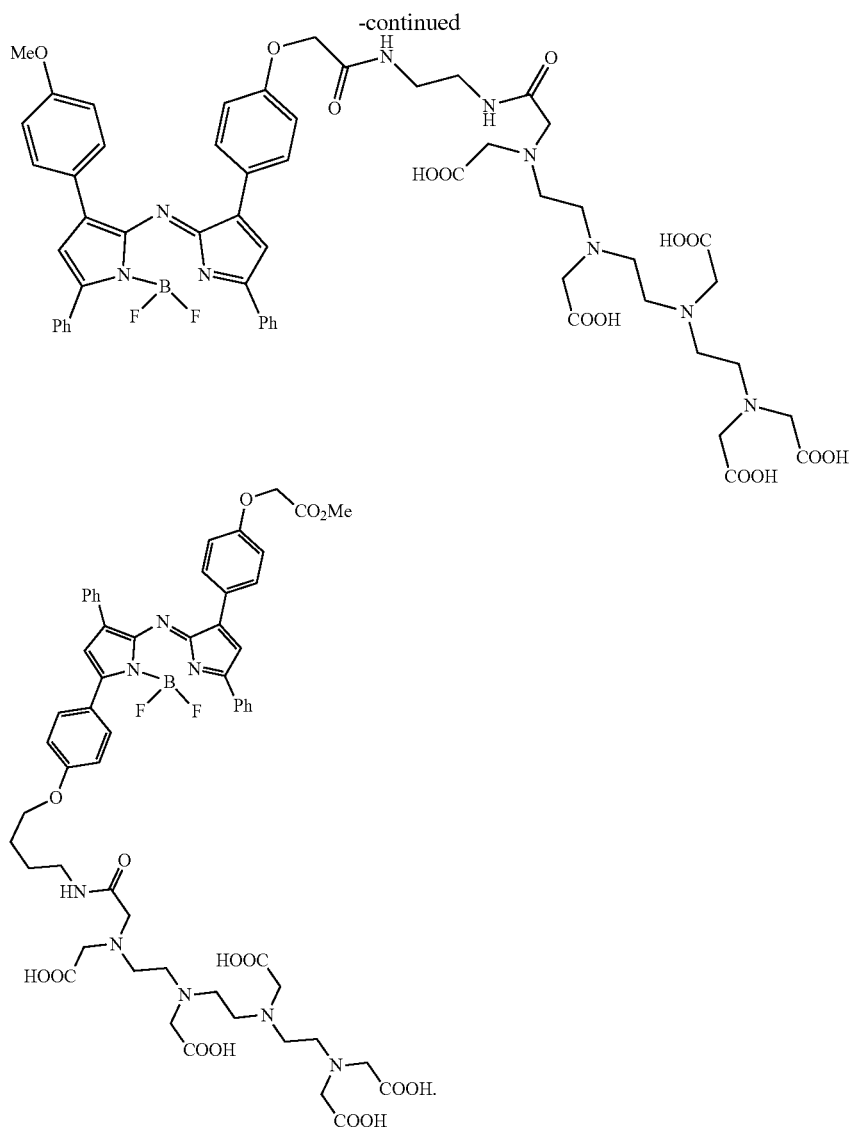
8. Complex according to claim 1, wherein the lanthanide is selected from the group consisting of: Yb, Nd, Ho, Tm, Sm, Dy, Eu, Pr, and Er.
9. A method of biological imaging comprising the steps of
1) providing a biological sample;
and 2) providing the fluorescent chromophore complex according to claim 1.
* * * * *